(12) United States Patent
Claussner et al.

(10) Patent No.: US 11,278,636 B2
(45) Date of Patent: Mar. 22, 2022

(54) OZONE DISINFECTING SYSTEM AND DEVICES CONFIGURED TO CONVERT WATER INTO OZONE FOR DISINFECTING, CLEANING, OR SANITIZING

(71) Applicant: Blue Penny LLC, Mooresville, NC (US)

(72) Inventors: Mark Claussner, Cornelius, NC (US); John Kazmer, Mooresville, NC (US)

(73) Assignee: Blue Penny LLC, Mooresville, NC (US)

( * ) Notice: Subject to any disclaimer, the term of this patent is extended or adjusted under 35 U.S.C. 154(b) by 0 days.

(21) Appl. No.: 17/137,867

(22) Filed: Dec. 30, 2020

(65) Prior Publication Data

US 2022/0023472 A1    Jan. 27, 2022

Related U.S. Application Data

(60) Provisional application No. 63/054,546, filed on Jul. 21, 2020.

(51) Int. Cl.
| | |
|---|---|
| *A61L 2/00* | (2006.01) |
| *A61L 9/00* | (2006.01) |
| *B08B 3/00* | (2006.01) |
| *A61L 2/18* | (2006.01) |
| *B08B 1/00* | (2006.01) |

(Continued)

(52) U.S. Cl.
CPC .............. *A61L 2/183* (2013.01); *A47K 10/38* (2013.01); *A47L 13/50* (2013.01); *A61L 2/26* (2013.01); *B08B 1/006* (2013.01); *C01B 13/10* (2013.01); *C11D 3/48* (2013.01); *C11D 11/0094* (2013.01); *C11D 17/049* (2013.01); *A61L 2101/02* (2020.08); *A61L 2202/11* (2013.01);

(Continued)

(58) Field of Classification Search
CPC ... A61L 2/00; A61L 2/183; A61L 2/24; A61L 2202/11; A61L 2202/16; A61L 2202/17; A61L 2202/20; C02F 1/78; C02F 2201/782; C02F 2303/04
USPC ................ 422/292, 305; 134/56 R, 184, 186
See application file for complete search history.

(56) References Cited

U.S. PATENT DOCUMENTS

| | | |
|---|---|---|
| 6,337,710 B1 | 1/2002 | Watkins et al. |
| 6,403,033 B1 | 6/2002 | Gutman |

(Continued)

FOREIGN PATENT DOCUMENTS

CN     104939723 A     9/2015

*Primary Examiner* — Monzer R Chorbaji
(74) *Attorney, Agent, or Firm* — Jeffrey C. Watson; Grell & Watson Patent Attorneys LLC

(57) ABSTRACT

An ozone disinfecting system includes a water holding tank configured to hold water for use by the ozone disinfecting system. An ozone generator machine is configured to convert the water into an ozone cleaner agent. An ozone holding tank is configured to hold the ozone cleaner agent created by the ozone generator machine. A drain is configured to drain fluid from the ozone holding tank to the water holding tank. A pump is configured to cycle the fluid from the water holding tank to the ozone generator machine and into the ozone holding tank. A controller is configured to control the pump, the ozone generator machine, and the drain. Wherein, the controller controls the pump, the ozone generator machine and the drain to create the ozone cleaner agent from the water and cycle it between the water holding tank and the ozone holding tank at a specified cycle time.

22 Claims, 10 Drawing Sheets

(51) Int. Cl.

| | |
|---|---|
| *C01B 13/10* | (2006.01) |
| *A47L 13/50* | (2006.01) |
| *A61L 2/26* | (2006.01) |
| *C11D 3/48* | (2006.01) |
| *C11D 11/00* | (2006.01) |
| *A47K 10/38* | (2006.01) |
| *C11D 17/04* | (2006.01) |
| *A61L 101/02* | (2006.01) |

(52) U.S. Cl.
CPC ....... *A61L 2202/14* (2013.01); *A61L 2202/17* (2013.01); *B08B 2203/005* (2013.01)

(56) References Cited

U.S. PATENT DOCUMENTS

| | | |
|---|---|---|
| 6,942,834 B2 | 9/2005 | Gutman |
| 9,380,920 B2 * | 7/2016 | Pollack ............... A47L 11/4083 |
| 9,969,632 B2 * | 5/2018 | Busick ...................... C02F 1/78 |
| 10,687,536 B2 | 6/2020 | Joshi |
| 2007/0278242 A1 * | 12/2007 | Amundson .......... A47K 10/421 |
| | | 221/63 |
| 2011/0085934 A1 | 4/2011 | Joshi et al. |
| 2013/0028787 A1 | 1/2013 | Takeuchi et al. |

\* cited by examiner

# OZONE DISINFECTING SYSTEM AND DEVICES CONFIGURED TO CONVERT WATER INTO OZONE FOR DISINFECTING, CLEANING, OR SANITIZING

CROSS-REFERENCE TO RELATED APPLICATIONS

This application claims the priority benefit of U.S. Provisional Application No. 63/054,546, filed on Jul. 21, 2020, entitled "O3 Oxidis Wipe Dispenser", which is incorporated by reference herein in its entirety.

FIELD OF THE DISCLOSURE

The present disclosure relates to disinfecting devices, systems, and methods configured for disinfecting, cleaning, sanitizing, wiping, the like, etc. Namely, the present disclosure is directed to providing disinfecting, cleaning, sanitizing, wiping, the like, etc. devices, systems and methods using ozone ("O3") created by using water ("H2O") (any). More specifically, the present disclosure is directed to providing disinfecting, cleaning, sanitizing, wiping, the like, etc. wipes, wipe dispensers, cleaning carts, the like, etc., using ozone created by using any water.

BACKGROUND

Generally speaking, disinfectants are chemical agents designed to inactivate or destroy microorganisms on inert surfaces. Disinfection does not necessarily kill all microorganisms, especially resistant bacterial spores, and is less effective than sterilization, which is an extreme physical or chemical process that kills all types of life. Disinfectants are generally distinguished from other antimicrobial agents such as antibiotics, which destroy microorganisms within the body, and antiseptics, which destroy microorganisms on living tissue. Disinfectants are also different from biocides, which are intended to destroy all forms of life, not just microorganisms. Disinfectants work by destroying the cell wall of microbes or interfering with their metabolism. It is also a form of decontamination, and can be defined as the process whereby physical or chemical methods are used to reduce the amount of pathogenic microorganisms on a surface.

Sanitizers are substances that simultaneously clean and disinfect. Disinfectants kill more germs than sanitizers. Disinfectants are frequently used in hospitals, dental surgeries, kitchens, and bathrooms to kill infectious organisms. Sanitizers are mild compared to disinfectants and are used majorly to clean things which are in human contact whereas disinfectants are concentrated and are used to clean surfaces like floors and building premises. Bacterial endospores are most resistant to disinfectants, but some fungi, viruses and bacteria also possess some resistance.

A wipe, also known as a wet towel or a moist towelette, disinfecting wipe, wet wipe, or a baby wipe in specific circumstances, is a small to medium-sized moistened piece of plastic or cloth that often comes folded and individually wrapped for convenience, or, in the case of dispensers, as a large roll with individual wipes that can be torn off. Wet wipes are used for cleaning purposes like personal hygiene and household cleaning. Ninety percent of wet wipes on the market are produced from nonwoven fabrics made of polyester or polypropylene that is moistened with water or other liquid chemicals (e.g., isopropyl alcohol) depending on the applications. The material may be treated with softeners, lotions, perfume and other chemicals to adjust the tactile and olfactory properties. Preservative chemicals, such as methylisothiazolinone, are used to prevent bacterial or fungal growth in the package. The finished wet wipes are folded and put in pocket size package or a box dispenser. Medical wet wipes are available for various applications. These include alcohol wet wipes, chlorhexidine wipes for disinfection of surfaces and noninvasive medical devices, and sporicidal wipes. Medical wipes can be used to prevent the spread of pathogens such as norovirus and COVID-19.

The instant disclosure recognizes the fact that most, if not all disinfectants, cleaners, wipes, the like, etc., use harsh chemicals, like volatile organic compounds ("VOC") to provide the disinfecting, cleaning, sanitizing, wiping effect desired. Volatile organic compounds are compounds that have a high vapor pressure and low water solubility. Many VOCs are human-made chemicals that are used and produced in the manufacture of paints, pharmaceuticals, and refrigerants. VOCs typically are industrial solvents, such as trichloroethylene; fuel oxygenates, such as methyl tert-butyl ether (MTBE); or by-products produced by chlorination in water treatment, such as chloroform. VOCs are often components of petroleum fuels, hydraulic fluids, paint thinners, and dry cleaning agents. VOCs are common ground-water contaminants. VOCs are emitted as gases from certain solids or liquids. VOCs include a variety of chemicals, some of which may have short- and long-term adverse health effects. Concentrations of many VOCs are consistently higher indoors (up to ten times higher) than outdoors. VOCs are emitted by a wide array of products numbering in the thousands. EPA's Office of Research and Development's "Total Exposure Assessment Methodology (TEAM) Study" (Volumes I through IV, completed in 1985) found levels of about a dozen common organic pollutants to be 2 to 5 times higher inside homes than outside, regardless of whether the homes were located in rural or highly industrial areas. TEAM studies indicated that while people are using products containing organic chemicals, they can expose themselves and others to very high pollutant levels, and elevated concentrations can persist in the air long after the activity is completed. As such, there is clearly a need to provide disinfecting devices, systems and methods configured for disinfecting, cleaning, sanitizing, wiping, the like etc. that uses less harsh chemicals or VOCs, or no harsh chemicals or VOCs at all.

In addition, the instant disclosure recognizes that these harsh chemicals, like VOCs, used in such disinfectants, cleaners, wipes, the like, etc. add to the cost of providing such disinfecting, cleaning, sanitizing, wiping, the like, etc. devices, systems and method. Thus, there is clearly an economic advantage to reduce or eliminate such harsh chemicals to lower the price and/or to increase revenue.

The instant disclosure also recognizes the waste and pollution created, not only from such harsh chemicals used in such disinfectants, cleaners, wipes, the like, etc., but also from the containers, packaging, bottles, the like etc. used to transport, sell, market, the like etc. such disinfectants, cleaners, wipes, the like, etc. Therefore, there is clearly an environmental need and benefit to reducing, not only the harsh chemicals used in such disinfectants, cleaners, wipes, the like, etc., but also the containers, packaging, bottles, the like, etc., used to transport, sell, market or the like, such disinfectants, cleaners, wipes, the like, etc.

The instant disclosure may be designed to address at least certain aspects of the problems or needs discussed above by providing ozone disinfecting systems and devices configured to convert water into ozone for disinfecting, cleaning, and/or sanitizing.

SUMMARY

Accordingly, in one aspect, the present disclosure embraces an ozone disinfecting system. The ozone disinfecting system may be configured for converting water into ozone for disinfecting, cleaning, sanitizing, the like, etc. The ozone disinfecting system may generally include a water holding tank, an ozone generator machine, an ozone holding tank, a drain, a pump, and a controller. The water holding tank may be configured to hold water for use by the ozone disinfecting system. The ozone generator machine may be configured to convert the water into an ozone cleaner agent. The ozone holding tank may be configured to hold the ozone cleaner agent created by the ozone generator machine. The drain may be configured to drain fluid from the ozone holding tank to the water holding tank. The pump may be configured to cycle the fluid from the water holding tank to the ozone generator machine, and into the ozone holding tank. Wherein, when the fluid is cycled, the fluid includes water moving from the water holding tank to the ozone generator machine, and the fluid includes the ozone cleaner agent moving from the ozone generator machine to the ozone cleaner holding tank. The controller may be configured to control the pump, the ozone generator machine, and the drain. Wherein, the controller controls the pump, the ozone generator machine and the drain to create the ozone cleaner agent from the water and cycle it between the water holding tank and the ozone holding tank at a specified cycle time.

One feature of the disclosed ozone disinfecting system may be that it can be configured for making the ozone cleaning agent anytime by just adding the water to the water holding tank.

Another feature of the disclosed ozone disinfecting system may be that the ozone cleaner agent created from the water by the ozone generator machine may be made with no chemicals or VOCs and may be configured for disinfecting, cleaning, sanitizing, or the like.

Another feature of the disclosed ozone disinfecting system may be that the ozone cleaner agent created from the water by the ozone generator machine may be configured to be 99.99% effecting for disinfecting, cleaning, sanitizing, or the like.

Another feature of the disclosed ozone disinfecting system may be that the specified cycle time that the ozone cleaning agent is created by cycling the fluid between the water holding tank and the ozone holding tank may be configured to maintain the ozone cleaning agent to be 99.99% effective for disinfecting, cleaning, sanitizing, or the like. In select embodiments of the disclosed ozone disinfecting system, the controller may include an adjustable timer configured to adjust the specified cycle time that the ozone cleaning agent is created by cycling the fluid between the water holding tank and the ozone holding tank. As examples, and clearly not limited thereto, the adjustable timer may be configured to adjust the specified cycle time between: every 30 minutes or more; every 15 minutes or more; every 10 minutes or more; every 5 minutes or more, the like, and/or combinations thereof.

In select embodiments of the disclosed ozone disinfecting system, the ozone disinfecting system may also include a wipe dispenser. The wipe dispenser may include a wipe holder housed in the ozone holding tank. The wipe holder may be configured to hold a plurality of wipes submerged in the ozone cleaning agent that is cycled through the ozone holding tank. Whereby, the ozone disinfecting system may be configured to maintain the plurality of wipes at 99.99% effective for disinfecting, cleaning, sanitizing, the like, etc.

In select embodiments of the disclosed ozone disinfecting system, the ozone disinfecting system may also include a spigot. The spigot may be in communication with the ozone holding tank. The spigot may be configured for removing the ozone cleaner agent from the ozone holding tank for filling a separate cleaning container with the ozone cleaning agent. In select embodiments, the spigot may be connected to a drain conduit. The drain conduit may be configured to move fluid from the drain of the ozone holding tank to the water holding tank. The separate cleaning containers filled from the spigot may be configured for aiding in disinfecting, cleaning, sanitizing, or the like, with the ozone cleaning agent. As examples, and clearly not limited thereto, the separate cleaning containers may include a bottle, a spray bottle, a bucket, a mop bucket, a basin, a container, the like, and/or combinations thereof.

In select embodiments of the disclosed ozone disinfecting system, a power source may be included. The power source may be configured to power the ozone disinfecting system, including, but not limited to, the controller, the pump, the drain, and the ozone generating machine. The power source may be, but is not limited to, a wired power source, a battery power source, the like, and combinations thereof.

In select embodiments of the disclosed ozone disinfecting system, the ozone disinfecting system may also include wiring. The wiring may be configured to provide communication between the power source, the controller, the pump, the ozone generating machine, and the drain.

In select embodiments of the disclosed ozone disinfecting system, the ozone disinfecting system may also include fluid lines. The fluid lines may be for moving and cycling the fluid (i.e. water, ozone, or mixtures thereof) back and forth between the water holding tank, the pump, the ozone generator machine, and the ozone holding tank. In select embodiments, the fluid lines may include a first fluid line, and a second fluid line. The first fluid line may be from approximate a bottom of the water holding tank to a pump inlet of the pump. The second fluid line may be from a pump outlet of the pump to an ozone generator inlet of the ozone generating machine. A nozzle may also be included in the ozone holding tank. The nozzle in the ozone holding tank may be configured to spray the ozone cleaner agent created by the ozone generating machine into the ozone holding tank, like for saturating the plurality of wipes positioned therein. The drain conduit may also be included. The drain conduit may be configured to move fluid from the drain of the ozone holding tank to the water holding tank via gravity.

In select embodiments of the disclosed ozone disinfecting system, the ozone disinfecting system may also include a stand. The stand may be configured to hold the water holding tank above the pump and the controller.

In select embodiments of the disclosed ozone disinfecting system, the ozone disinfecting system may be configured for and incorporated in a self-contained mobile wipe dispenser unit. The self-contained mobile wipe dispenser unit may be configured for dispensing sanitizing wipes soaked in the ozone cleaner agent cycled through the ozone holding tank.

In select embodiments of the disclosed ozone disinfecting system, the ozone disinfecting system may be configured for and incorporated in a self-contained mobile cleaning cart. The self-contained mobile cleaning cart may be configured for providing the ozone cleaner agent to separate cleaning containers, for dispensing sanitizing wipes, the like, or combinations thereof.

In another aspect, the instant disclosure embraces a self-contained mobile wipe dispenser unit. The self-contained mobile wipe dispenser may generally include the disclosed ozone disinfecting system in any of the various embodiments and/or combinations of embodiments shown and/or described herein. Accordingly, the ozone disinfecting system of the self-contained mobile wipe dispenser may generally include a water holding tank, an ozone generator machine, an ozone holding tank, a drain, a pump, and a controller. The water holding tank may be configured to hold water for use by the ozone disinfecting system. The ozone generator machine may be configured to convert the water into an ozone cleaner agent. The ozone holding tank may be configured to hold the ozone cleaner agent created by the ozone generator machine. The drain may be configured to drain fluid from the ozone holding tank to the water holding tank. The pump may be configured to cycle the fluid from the water holding tank to the ozone generator machine, and into the ozone holding tank. Wherein, when the fluid is cycled, the fluid includes water moving from the water holding tank to the ozone generator machine, and the fluid includes the ozone cleaner agent moving from the ozone generator machine to the ozone cleaner holding tank. The controller may be configured to control the pump, the ozone generator machine, and the drain. Wherein, the controller controls the pump, the ozone generator machine and the drain to create the ozone cleaner agent from the water and cycle it between the water holding tank and the ozone holding tank at a specified cycle time.

In select embodiments of the disclosed self-contained mobile wipe dispenser unit, the self-contained mobile wipe dispenser may also include a wipe dispenser. The wipe dispenser may include a wipe holder. The wipe holder may be housed in the ozone holding tank. The wipe holder may be configured to hold a plurality of wipes. The plurality of wipes may be submerged in the ozone cleaning agent that is cycled through the ozone holding tank. Whereby, the plurality of wipes may be configured to be maintained at 99.99% effective for disinfecting, cleaning, sanitizing, the like, etc.

In select embodiments of the disclosed self-contained mobile wipe dispenser unit, the self-contained mobile wipe dispenser may also include a housing. The housing may be configured for housing the ozone disinfecting system inside of the self-contained mobile wipe dispenser unit. The housing may include a substantially cylindrically shaped vessel. The substantially cylindrically shaped vessel may have an open top and a closed bottom. The ozone disinfecting system may be positioned on the closed bottom inside of the substantially cylindrically shaped vessel. An access door may be included in the substantially cylindrically shaped vessel. The access door may be configured for accessing the ozone disinfecting system inside of the substantially cylindrically shaped vessel. A shelf may be included inside of the substantially cylindrically shaped vessel. The shelf may be configured to hold the ozone holding tank inside of the substantially cylindrically shaped vessel in a position where a top of the ozone holding tank is positioned approximate the open top of the substantially cylindrically shaped vessel. A removable lid may also be included. The removable lid may be configured for covering the open top of the substantially cylindrically shaped vessel. The removable lid may be configured to be removed for accessing the wipe dispenser and ozone holding tank positioned on the shelf. The removable lid may include a wipe opening configured for pulling one of the plurality of wipes at a time from the wipe dispenser.

In select embodiments of the disclosed self-contained mobile wipe dispenser unit, the self-contained mobile wipe dispenser may also include a spigot. The spigot may be in communication with the ozone holding tank. The spigot may be configured for removing the ozone cleaner agent from the ozone holding tank for filling separate cleaning containers with the ozone cleaning agent. The spigot may be positioned where it can be accessed through the access door of the substantially cylindrically shaped vessel.

In select embodiments of the disclosed self-contained mobile wipe dispenser unit, the self-contained mobile wipe dispenser may also include a power source. The power source may be configured to power the disclosed self-contained mobile wipe dispenser unit, including, but not limited to, the controller, the pump, the drain, and the ozone generating machine of the ozone disinfecting system.

One feature of the disclosed self-contained mobile wipe dispenser unit may be that it can be configured for dispensing sanitizing wipes soaked in the ozone cleaner agent cycled through the ozone holding tank.

In another aspect, the instant disclosure embraces a self-contained mobile cleaning cart. The self-contained mobile cleaning cart may generally include the disclosed ozone disinfecting system in any of the various embodiments and/or combinations of embodiments shown and/or described herein. Accordingly, the ozone disinfecting system of the self-contained mobile cleaning cart may generally include a water holding tank, an ozone generator machine, an ozone holding tank, a drain, a pump, and a controller. The water holding tank may be configured to hold water for use by the ozone disinfecting system. The ozone generator machine may be configured to convert the water into an ozone cleaner agent. The ozone holding tank may be configured to hold the ozone cleaner agent created by the ozone generator machine. The drain may be configured to drain fluid from the ozone holding tank to the water holding tank. The pump may be configured to cycle the fluid from the water holding tank to the ozone generator machine, and into the ozone holding tank. Wherein, when the fluid is cycled, the fluid includes water moving from the water holding tank to the ozone generator machine, and the fluid includes the ozone cleaner agent moving from the ozone generator machine to the ozone cleaner holding tank. The controller may be configured to control the pump, the ozone generator machine, and the drain. Wherein, the controller controls the pump, the ozone generator machine and the drain to create the ozone cleaner agent from the water and cycle it between the water holding tank and the ozone holding tank at a specified cycle time.

In select embodiments of, the self-contained mobile cleaning cart, the self-contained mobile cleaning cart may also include a cart device. The cart device may be configured for housing the ozone disinfecting system. The cart device may generally include a base with a plurality of wheels attached thereto configured for rolling the cart device. An enclosure may be positioned on the base. The enclosure may be sized and configured for enclosing the ozone disinfecting system. In select embodiments, the enclosure may include a front door, a back door, and/or a top frame. The front door may be configured for accessing the ozone disinfecting system. The back door may also be configured for accessing the ozone disinfecting system. The top frame may have an opening, a top lid, and a plurality of mounts. The top lid may be configured to be opened for accessing the ozone holding tank of the ozone disinfecting system through the opening. The opening of the top frame may configured to hold the ozone holding tank in a position above the water holding tank, where a lip of the ozone holding tank may fit on top of the top frame and around the opening. The plurality of mounts of the top frame may be configured for mounting cleaning accessories, like, but clearly not limited thereto, a bottle, a spray bottle, a mop, a basin, a container, the like, or a combination thereof.

In select embodiments of the self-contained mobile cleaning cart, a drawer may be included. The drawer may be positioned below the base. The drawer may be configured for housing the controller of the ozone disinfecting system.

In select embodiments of the self-contained mobile cleaning cart, a spigot may be included. The spigot may be in communication with the ozone holding tank. The spigot may be configured for removing the ozone cleaner agent from the ozone holding tank for filling the separate cleaning containers with the ozone cleaning agent. The spigot may be positioned through the enclosure where it can be accessed outside of the enclosure.

In select embodiments of the self-contained mobile cleaning cart, a mop bucket may be included. The mop bucket may be positioned on the base on a first side of the enclosure.

In select embodiments of the self-contained mobile cleaning cart, a spare water tank may be included. The spare water tank may be positioned on the base on a second side of the enclosure. The spare water tank may be configured to hold extra of the water for the ozone disinfecting system.

In select embodiments of the self-contained mobile cleaning cart, power source may be included. The power source may be configured to power the self-contained mobile cleaning cart, including, but not limited to, the controller, the pump, the drain, and the ozone generating machine of the ozone disinfecting system.

In another aspect, the present disclosure embraces a method of making an ozone cleaner agent in any of the various embodiments and/or combination of embodiments shown and/or described herein.

In another aspect, the present disclosure embraces a method of making disinfecting wipes in any of the various embodiments and/or combination of embodiments shown and/or described herein.

The terminology used herein is for the purpose of describing particular embodiments only and is not intended to be limiting of the disclosure. As used herein, the term "and/or" includes any and all combinations of one or more of the associated listed items. As used herein, the singular forms "a", "an" and "the" are intended to include the plural forms as well as the singular forms, unless the contest clearly indicates otherwise. It will be further understood that the terms "compromises" and/or "comprising" when used in this specification, specify the presence of stated features, steps, operations, elements and/or components, but do not preclude the presence of addition of one or more other features, steps, operations, elements, components and/or groups thereof.

Unless otherwise defined, all terms (including technical and scientific terms) used herein have the same meaning as commonly understood by one having ordinary skill in the art to which this disclosure belongs. It will be further understood that terms, such as those defined in commonly used dictionaries, should be interpreted as having a meaning that is consistent with their meaning in the context of the relevant art and the present disclosure and will not be interpreted in an idealized or overly formal sense unless expressly so defined herein.

In describing the disclosure, it will be understood that a number of enhancements are disclosed. Each of these has individual benefit, and each can also be used in conjunction with one or more, or in some cases all, of the other disclosed techniques. Accordingly, for the sake of clarity, the description will refrain from repeating every possible combination of the individual steps in an unnecessary fashion. Nevertheless, the specification and claims should be read with the understanding that such combinations are entirely within the scope of the disclosure and the claims.

It will be evident, however, to one skilled in the art, that the present disclosure may be practiced without specific details.

The present disclosure is to be considered as an exemplification of the disclosure, and is not intended to limit the disclosure to the specific embodiments illustrated by the figures or description below.

The foregoing illustrative summary, as well as other exemplary objectives and/or advantages of the disclosure, and the manner in which the same are accomplished, are further explained within the following detailed description and its accompanying drawings.

BRIEF DESCRIPTION OF THE DRAWINGS

The present disclosure will be better understood by reading the Detailed Description with reference to the accompanying drawings, which are not necessarily drawn to scale, and in which like reference numerals denote similar structure and refer to like elements throughout, and in which.

Figure 1:
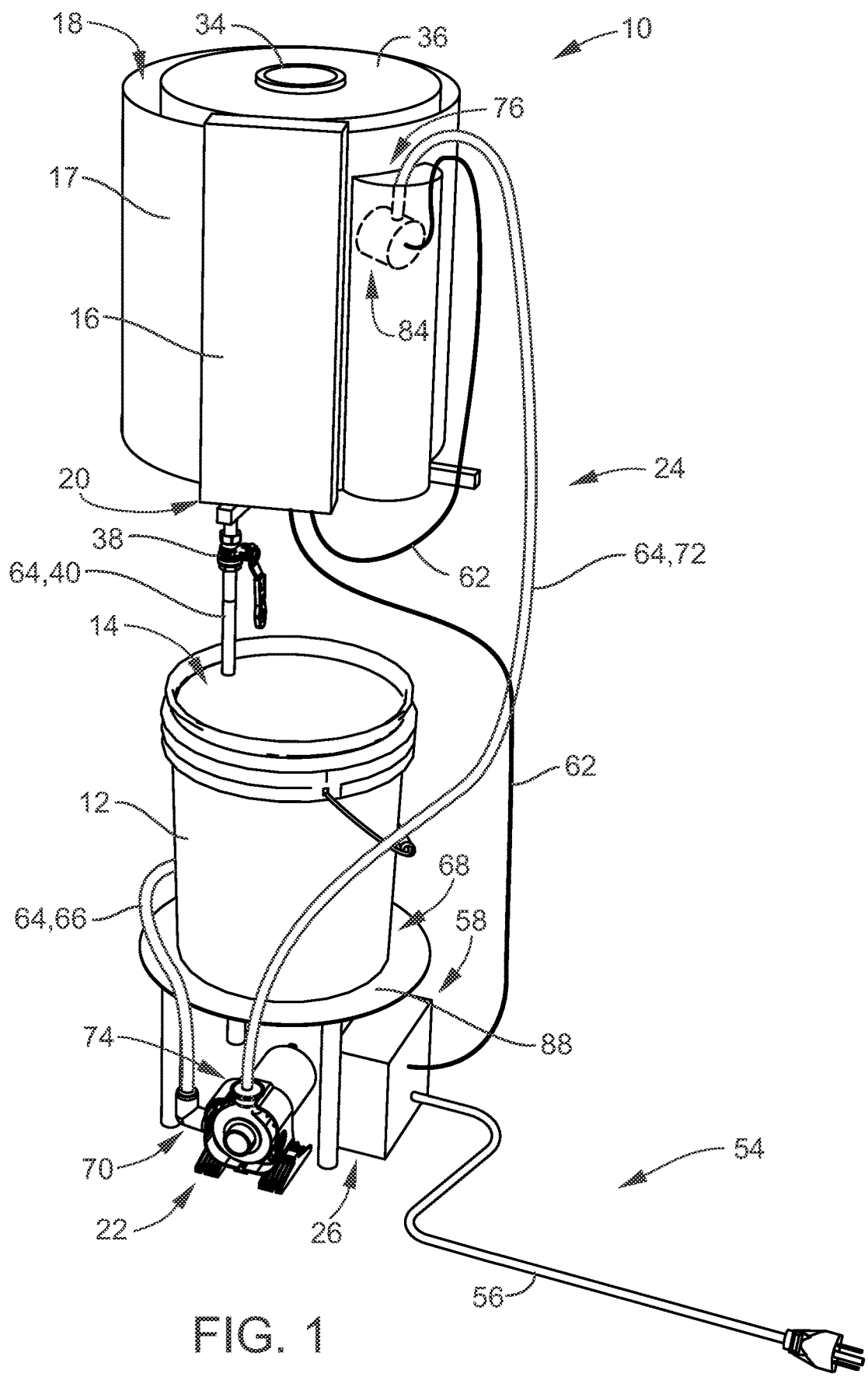
FIG. 1 is a side perspective view of an ozone disinfecting system configured to convert water into ozone for disinfecting, cleaning, and/or sanitizing according to select embodiments of the instant disclosure.
Figure 2:
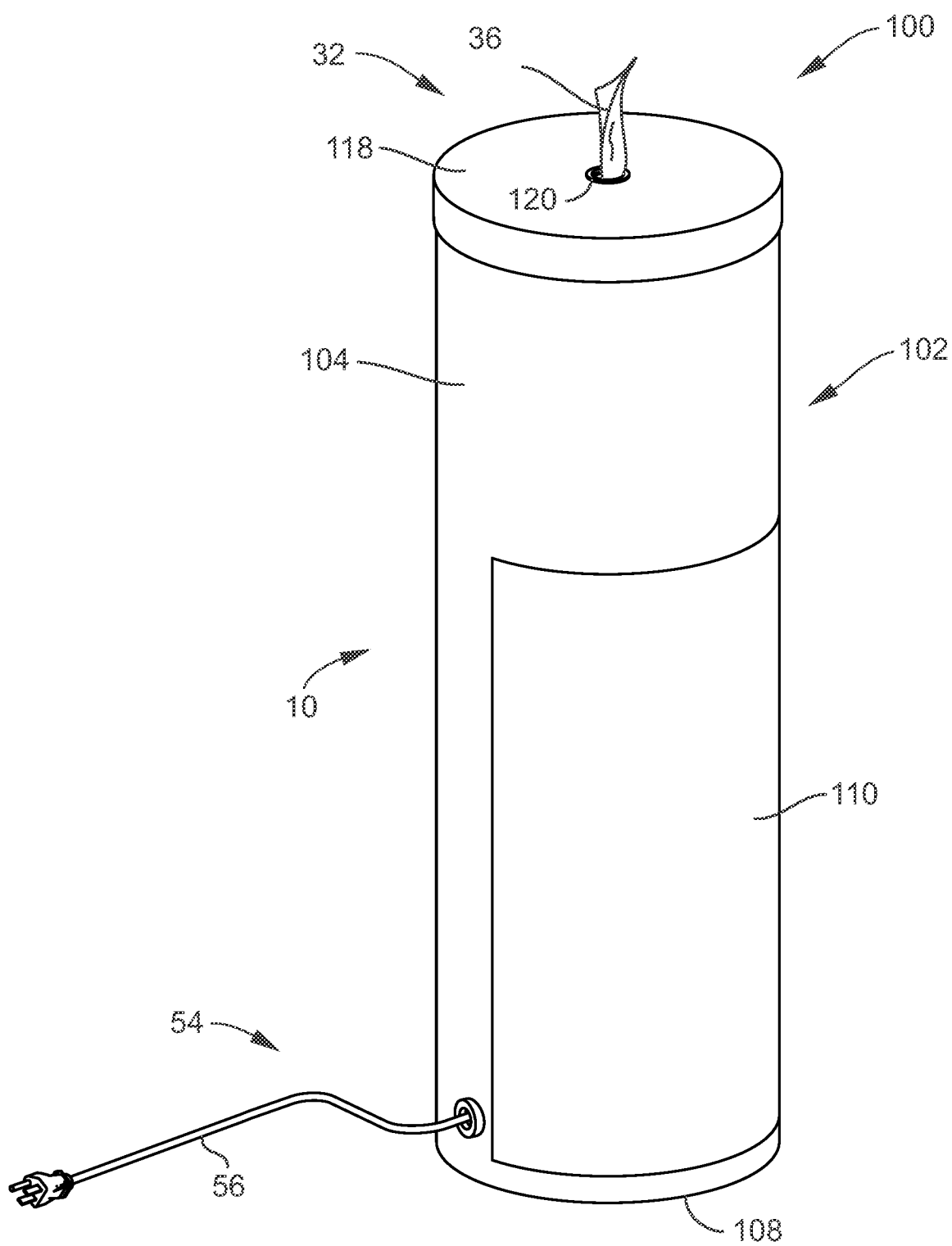
FIG. 2 is a side perspective view of a wipe dispenser according to select embodiments of the instant disclosure configured to house the ozone disinfecting system of FIG. 1.
Figure 3:
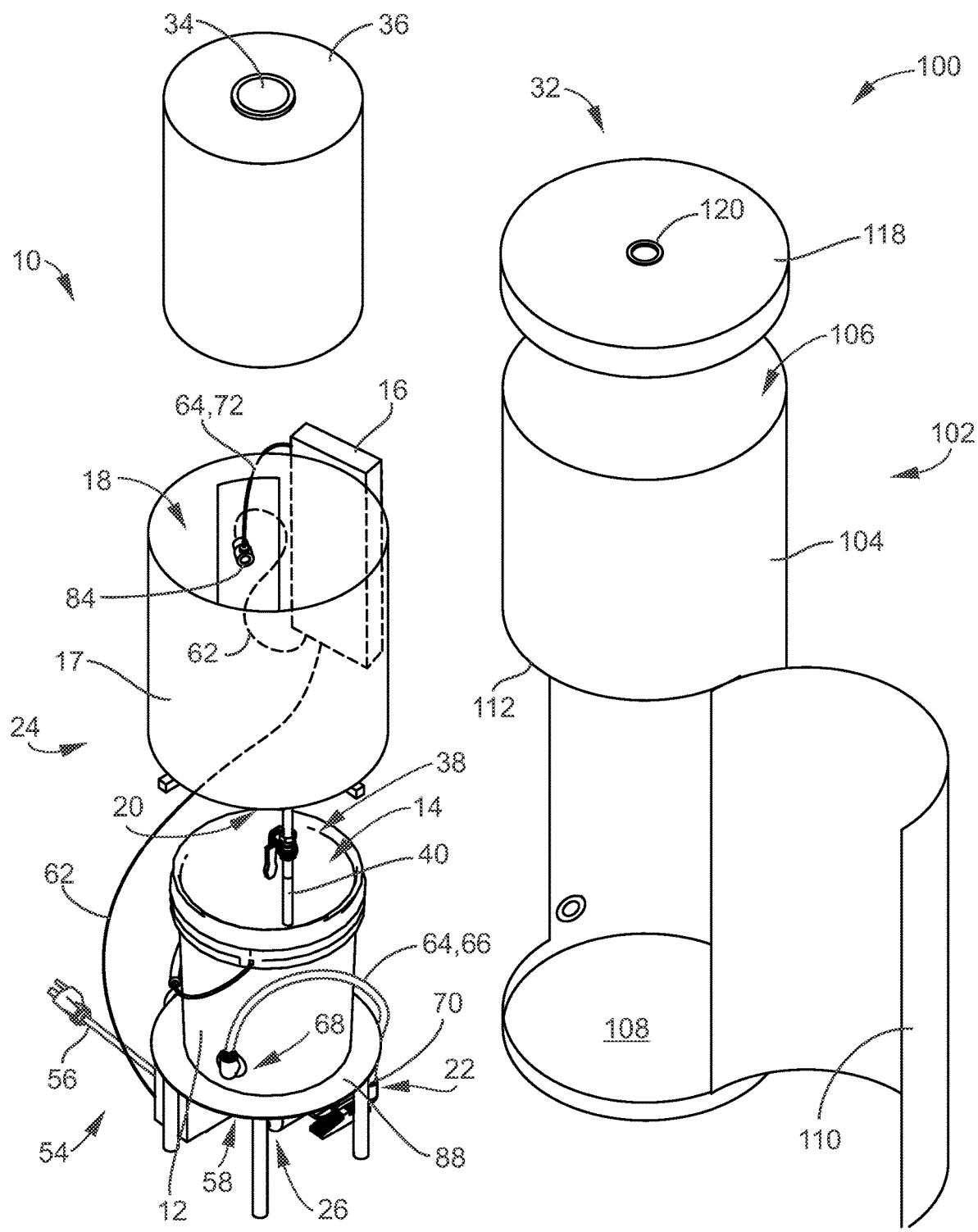
FIG. 3 is a top side perspective view of the ozone disinfecting system from FIG. 1 shown partially disassembled from the wipe dispenser of FIG. 2.
Figure 4:
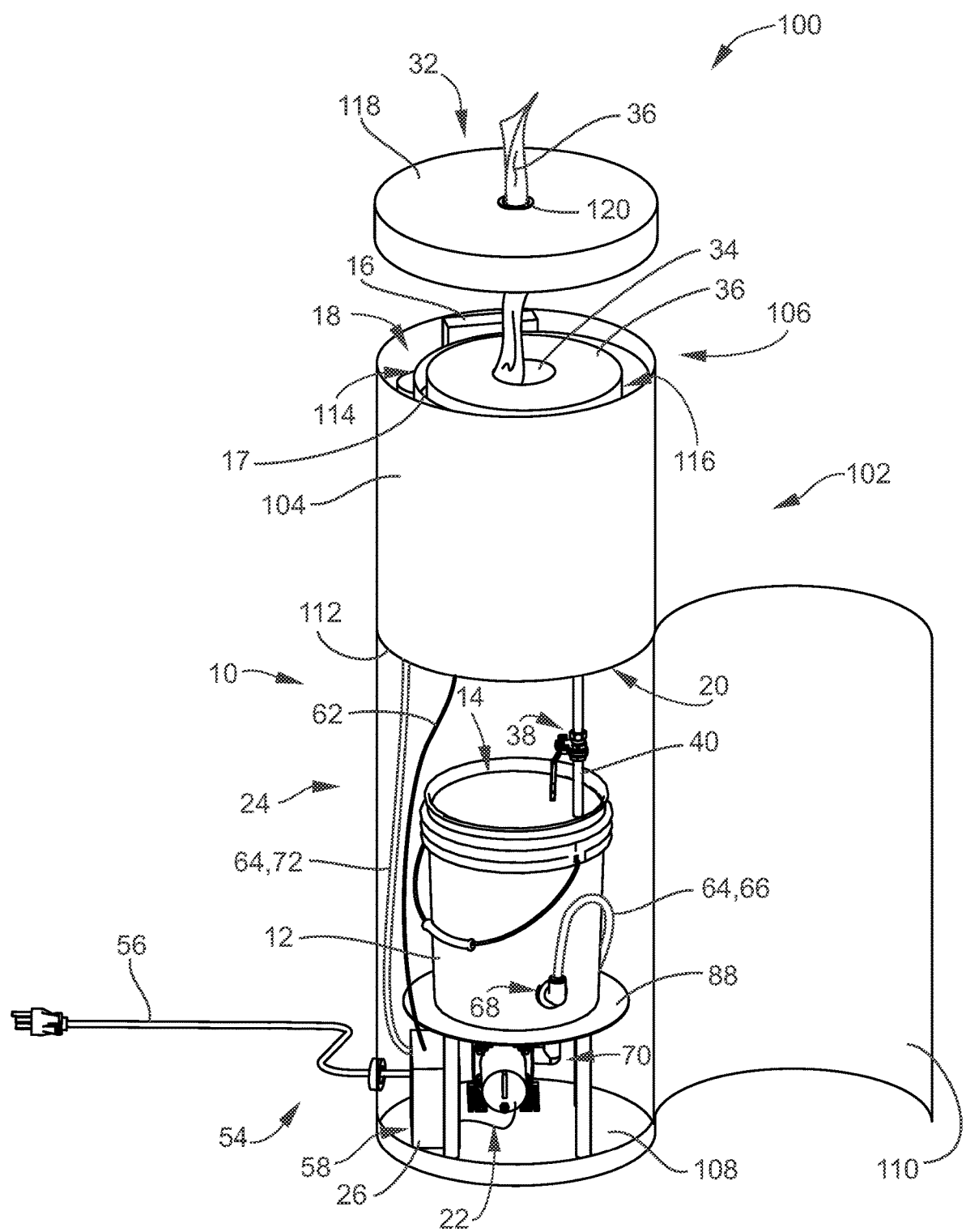
FIG. 4 is a side perspective view of the wipe dispenser from FIG. 2 with the ozone disinfecting system of FIG. 1 incorporated therein, with the access door open showing the ozone disinfecting system inside of the wipe dispenser, and the wipe dispenser lid partially removed to show the wipes.
Figure 5:
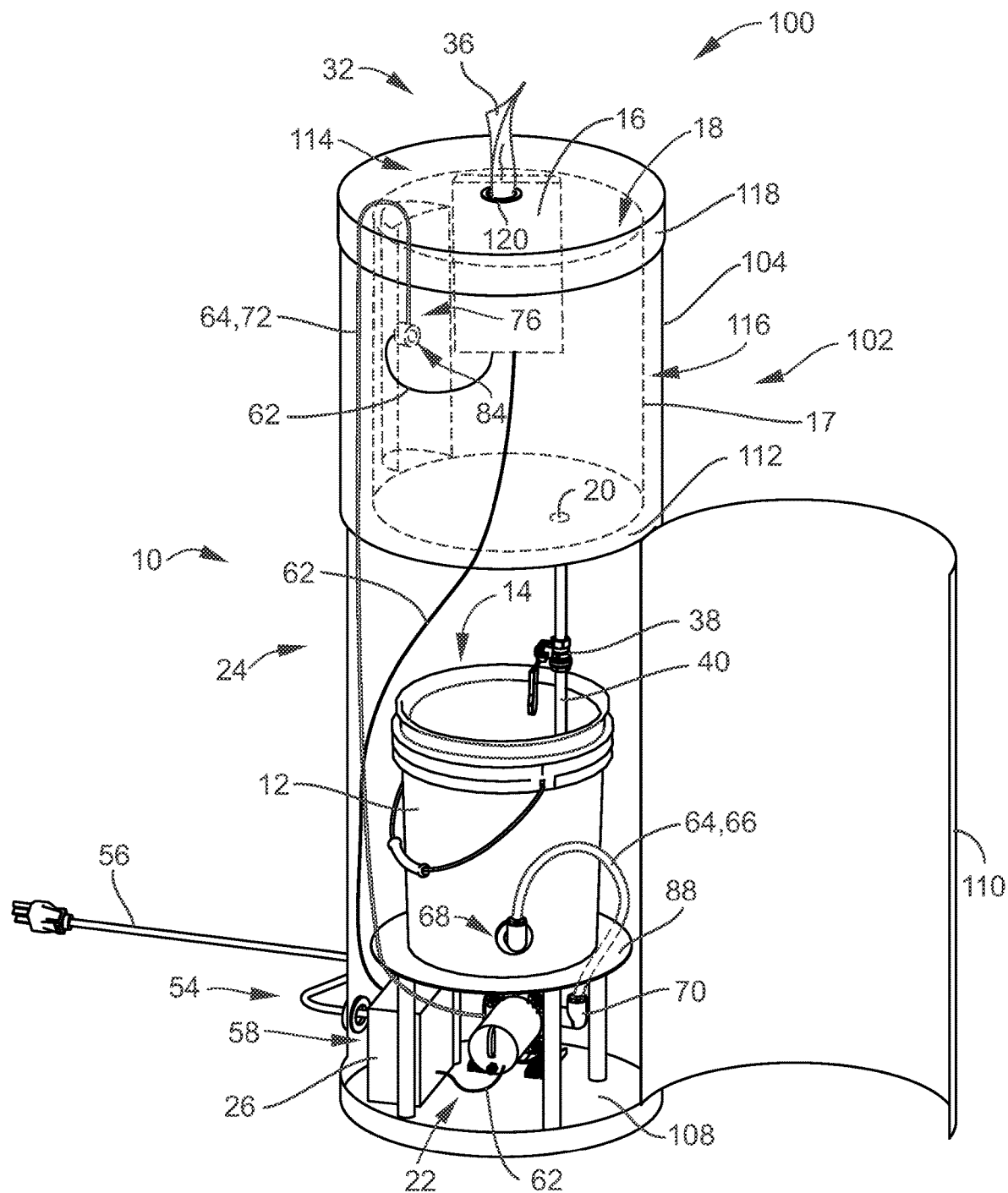
FIG. 5 is another side perspective view of the wipe dispenser from FIG. 2 with the ozone disinfecting system of FIG. 1 incorporated therein, with the access door open showing the ozone disinfecting system inside of the wipe dispenser, and showing the internal components of the wipe dispenser.
Figure 6:
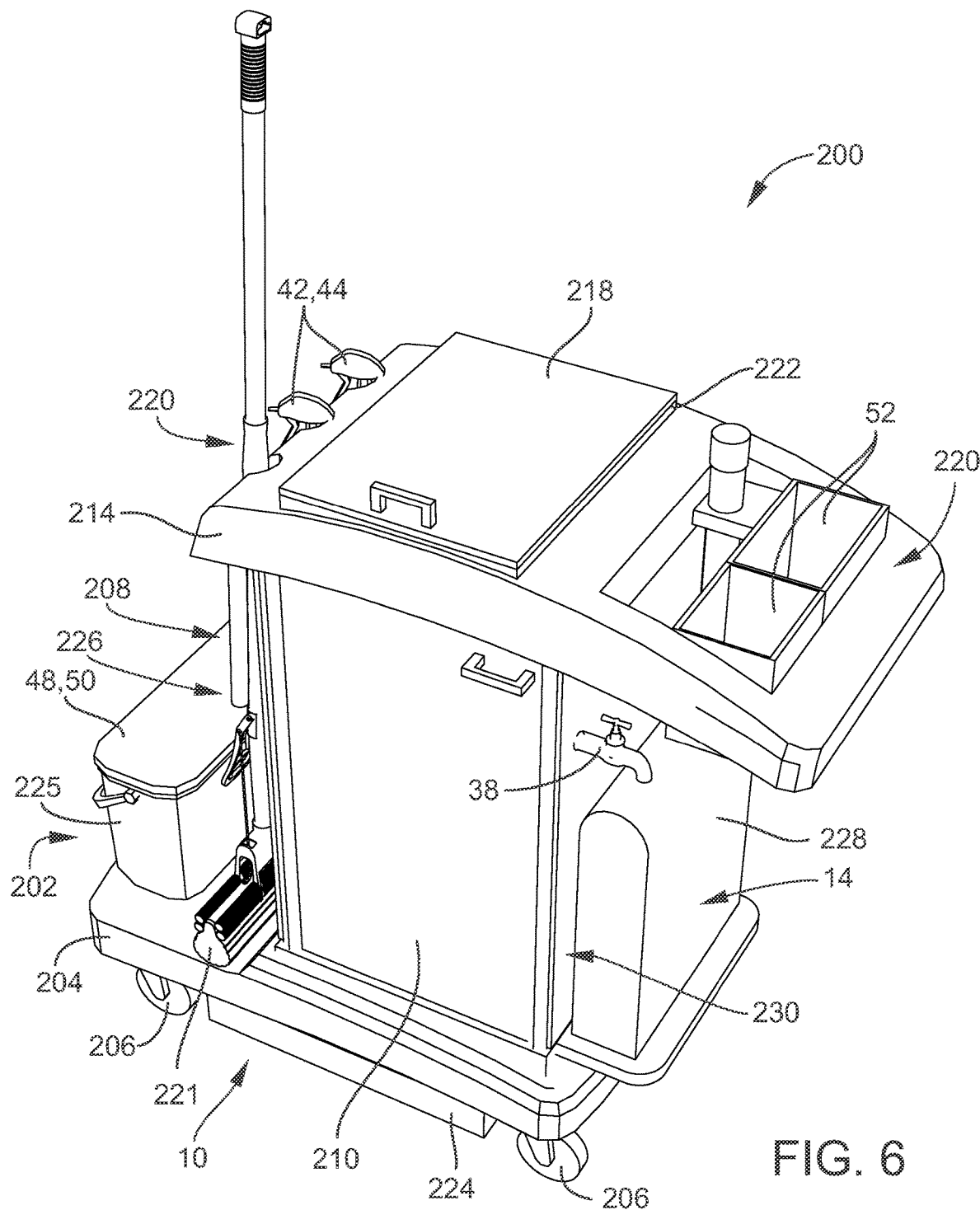
FIG. 6 is a front side, top perspective view of a cleaning cart ozone disinfecting system according to select embodiments of the instant disclosure configured to house an ozone disinfecting system according to select embodiments of the instant disclosure, with the ozone disinfecting system housed therein.
Figure 7:
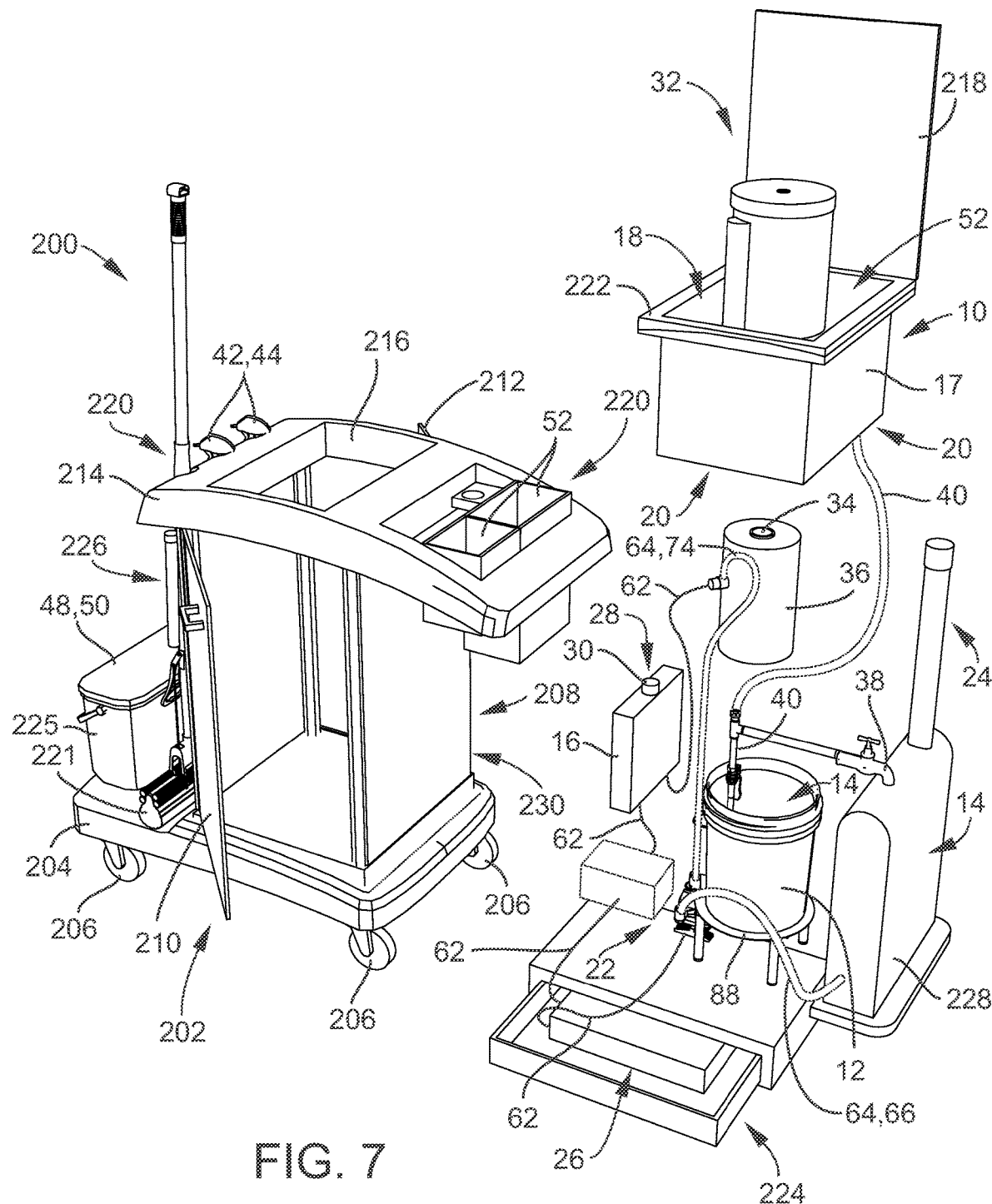
FIG. 7 is a front side, top perspective view of the cleaning cart from FIG. 6, showing the ozone disinfecting system partially disassembled from the cleaning cart.
Figure 8:
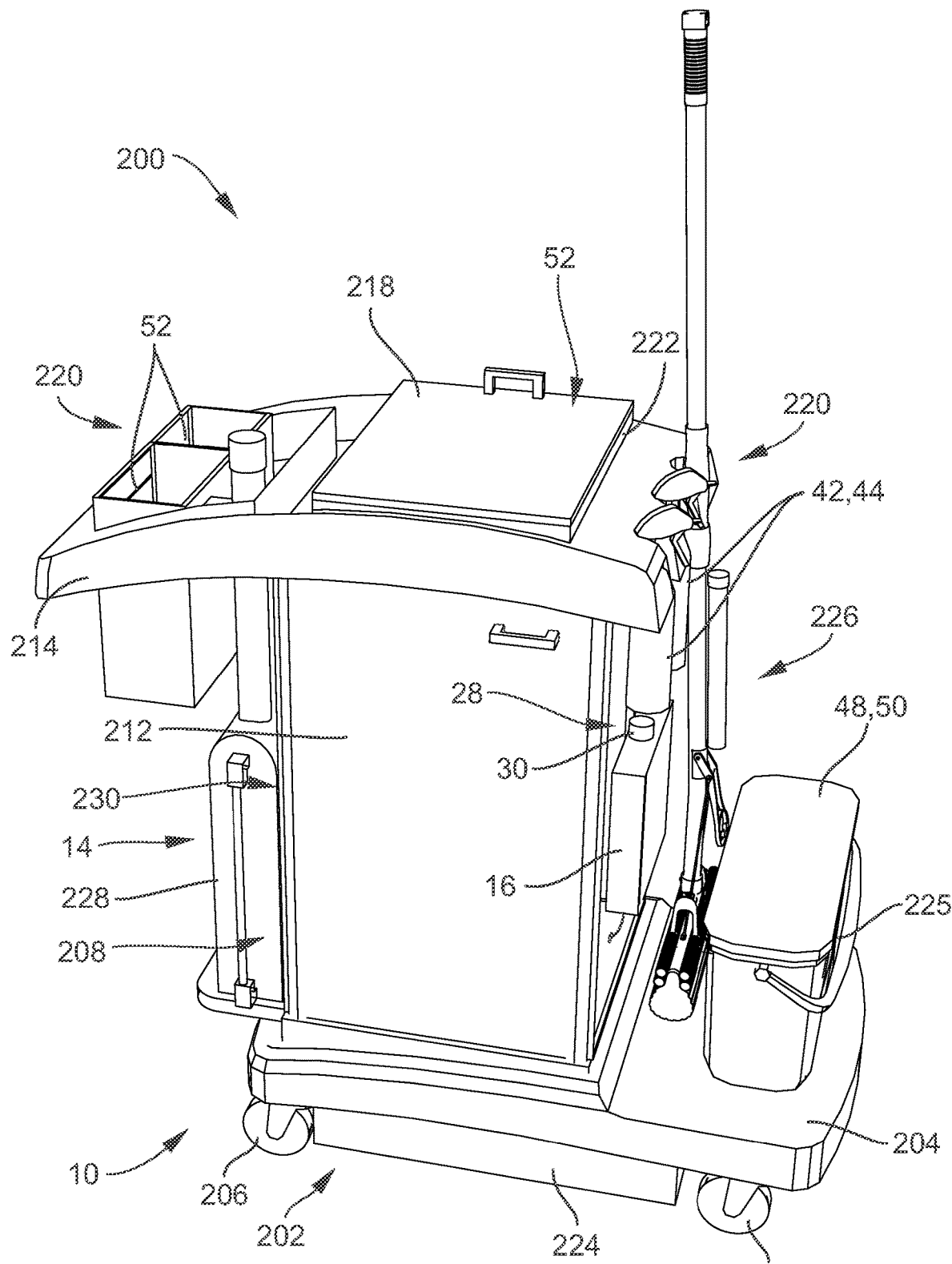
FIG. 8 is a back side, top perspective view of the cleaning cart from FIG. 6 with the ozone disinfecting system housed therein.
Figure 9:
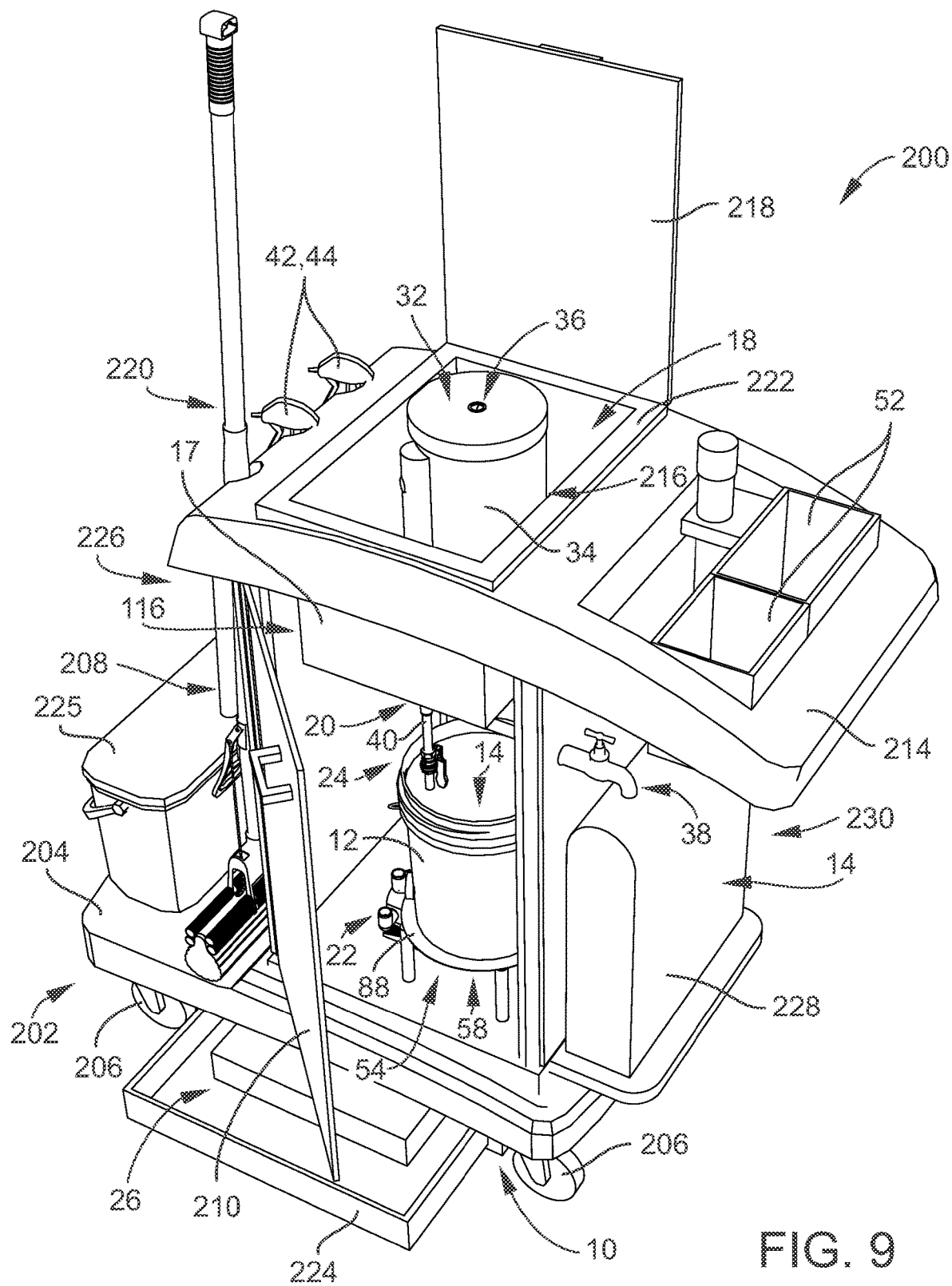
FIG. 9 is another front side, top perspective view of the cleaning cart from FIG. 6 with the front door open showing the ozone disinfecting system housed therein, and the top lid open showing the wipe dispenser component.
Figure 10:
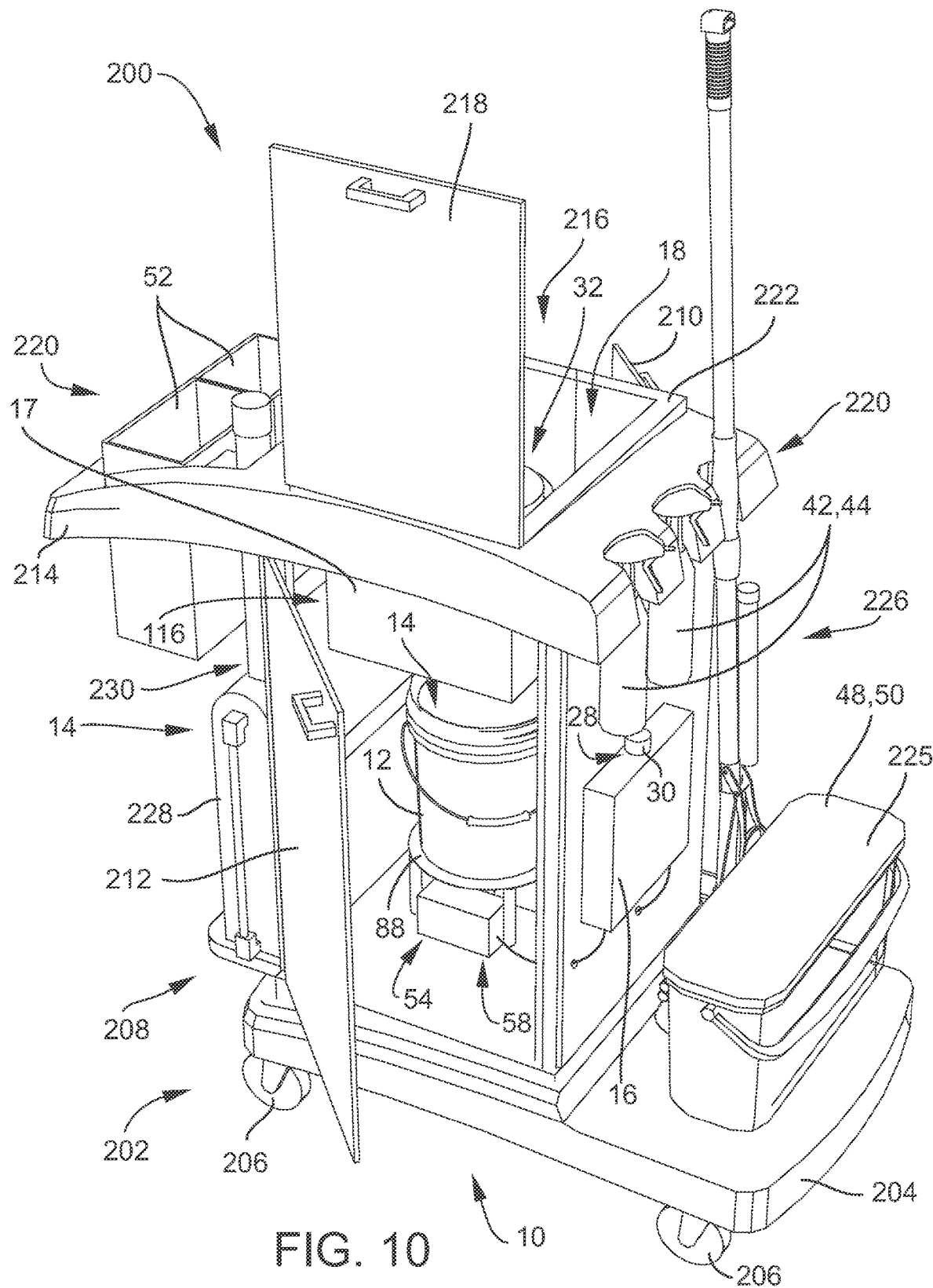
FIG. 10 is another back side, top perspective view of the cleaning cart from FIG. 6 with the back door open showing the ozone disinfecting system housed therein, and the top lid open showing the wipe dispenser component.

It is to be noted that the drawings presented are intended solely for the purpose of illustration and that they are, therefore, neither desired nor intended to limit the disclosure to any or all of the exact details of construction shown, except insofar as they may be deemed essential to the claimed disclosure.

DETAILED DESCRIPTION

Referring now to FIGS. 1-10, in describing the exemplary embodiments of the present disclosure, specific terminology is employed for the sake of clarity. The present disclosure, however, is not intended to be limited to the specific terminology so selected, and it is to be understood that each specific element includes all technical equivalents that operate in a similar manner to accomplish similar functions. Embodiments of the claims may, however, be embodied in many different forms and should not be construed to be limited to the embodiments set forth herein. The examples set forth herein are non-limiting examples and are merely examples among other possible examples. The present disclosure may solve the aforementioned limitations of the currently available devices and methods of storage by providing ozone disinfecting system 10. Ozone disinfecting system 10 may be used for creating ozone from any water that is effective for disinfecting, cleaning, sanitizing, wiping, the like, etc. Accordingly, the present disclosure of ozone disinfecting system 10 solves the aforementioned limitations of the currently available cleaning, sanitizing, disinfecting, wiping, the like, etc. devices, systems and methods by providing ozone disinfecting system 10 that may provide a 99.99% effective ozone cleaning agent 18 or solution by merely adding water. Ozone cleaning agent 18 created by ozone disinfecting system 10 may be an effective disinfectant, sanitizer, cleaner, wiper, the like etc. that does not include any harsh chemicals, including, but not limited to, not including any VOCs. One feature of the disclosed ozone disinfecting system 10 may be that it can be configured for making ozone cleaning agent 18 at anytime and at any place by just adding water 14 to water holding tank 12 and powering the system. Another feature of the disclosed ozone disinfecting system 10 may be that ozone cleaner agent 18 created from water 14 by ozone generator machine 16 may be made with no chemicals or VOCs and may be configured for disinfecting, cleaning, sanitizing, or the like.

Referring now to FIG. 1, ozone disinfecting system may generally include water holding tank 12, ozone generator machine 16, ozone holding tank 17, drain 20, pump 22, and controller 26. These parts and their operations will be described in detail below.

Water holding tank 12 may be included with ozone disinfecting system 10. See FIGS. 1, 3, 4, 5, 7, 9, and 10. Water holding tank 12 may be configured to hold water 14 for use by ozone disinfecting system 10. Water 14 held or filled into water holding tank 12 may be any water, like tap water, bottled water, distilled water, the like, etc. Water 14 may be manually filled into water holding tank 12 by any means, including manually, or automatically filled into water holding tank 12. Water holding tank 12 may be any device designed to hold water, including any desired size or shape. As an example, and clearly not limited thereto, as shown in the Figures, water holding tank 12 may be a 5 gallon bucket or the like. The 5 gallon bucket may include a handle to aid a user in removing and manually filling water holding tank 12. Or, a hose may be run into water holding tank 12 for filling water holding tank 12. Water holding tank 12 may also be hooked up to a water source, whereby water holding tank 12 may be continuously and/or automatically filled.

Ozone generator machine 16 may be included with ozone disinfecting system 10. See FIGS. 1, 3, 4, 5, 7, 8 and 10. Ozone generator machine 16 may be configured to convert water 14 into ozone cleaner agent 18. Ozone generator machine 16 may be any device or system configured for converting water 14 into ozone cleaner agent 18. Ozone generator machine 16 may be an ozonator type device. As an example, and clearly not limited thereto, ozone generator machine 16 may be an ozonator machine produced by Geann Industrial Co., Ltd. of Taiwan as used in faucets provided by Kona® Green Faucet of Florence, S.C.

Ozone holding tank 17 may be included in ozone disinfecting system 10. See FIGS. 1, 3, 4, 5 7, 9 and 10. Ozone holding tank 17 may be configured to hold ozone cleaner agent 18 created by the ozone generator machine 16. Ozone holding tank 17 may be any device designed to hold ozone cleaner agent 18, including any desired size or shape. As an example, and clearly not limited thereto, as shown in the Figures, ozone holding tank 17 may be cylindrically shaped tank or bucket configured to hold ozone cleaner agent 18.

Drain 20 may be included in ozone disinfecting system 10. See FIGS. 1, 3, 4, 5, 7 and 9. Drain 20 may be configured to drain fluid 24 (water 14, ozone cleaner agent 18, or mixtures thereof) from ozone holding tank 17 to water holding tank 12. Drain 20 may be any device or drain configured to move fluid 24 from ozone holding tank 17 to water holding tank 12. In select embodiments, as shown in the Figures, drain 20 may be positioned on the bottom of ozone holding tank 17, whereby gravity may be utilized for moving fluid from ozone holding tank 17 to water holding tank 12. Drain 20 may include a valve or the like configured for opening and closing the drain and controlling the flow of fluid 24 from ozone holding tank 17 into water holding tank 12.

Pump 22 may be included with ozone disinfecting system 10. See FIGS. 1, 3, 4, 5, 7, and 9. Pump 22 may be configured to cycle fluid 24 from water holding tank to ozone generator machine 16, and into ozone holding tank 17. When fluid 24 is cycled via pump 22, fluid 24 may include water 14 moving from water holding tank 12 to ozone generator machine 16, and fluid 24 may include ozone cleaner agent 18 moving from ozone generator machine 16 to ozone cleaner holding tank 17.

Controller 26 may be included with ozone disinfecting system 10. See FIGS. 1, 3, 4, 5, 7, and 9. Controller 26 may be configured to control ozone disinfecting system 10, including, but not limited to, pump 22, ozone generator machine 16, and drain 20. Controller 26 may include any device, devices, means, mechanisms, computers, controllers, the like, etc., configured to control ozone disinfecting system 10. Controller 26 may control pump 22, ozone generator machine 16 and drain 20 to create ozone cleaner agent 18 from water 14 and cycle it between water holding tank 12 and ozone holding tank 17 at specified cycle time 28. It is important to note that, once ozone cleaner agent 18 is created via ozone generator machine 16, ozone cleaner agent 18 has a short shelf life as a disinfectant, cleaner, sterilizer, wipe, the like etc. as ozone cleaner agent 18 may become less effective and convert back to water 14. The shelf life of ozone cleaner agent 18 may be on average of around 30 minutes. Thus, it may be necessary for controller 26 to cycle fluid 24 through ozone disinfecting system 10 at least every 30 minutes to maintain its effectiveness. In select embodiments of ozone disinfecting system 10, controller 26 may include adjustable timer 30 configured to adjust specified cycle time 28 that ozone cleaning agent 18 is created by cycling fluid 24 between water holding tank 12 and ozone holding tank 17. As examples, and clearly not limited thereto, adjustable timer 30 may be configured to adjust specified cycle time 28 between, but not limited to: every 30 minutes or more; possibly preferably every 15 minutes or more; possibly even more preferably every 10 minutes or more; and possibly most preferable every 5 minutes or more, the like, and/or combinations thereof.

Ozone cleaner agent 18 may be created by the disclosed ozone disinfecting system 10. See FIGS. 1, 3, 4, 5, 7, 9 and 10. Ozone cleaner agent 18 may be an ozone, O3, or $O_3$ liquid or fluid created from water. Ozone disinfecting system 10 may be designed, sized and configured to make various quantities of ozone cleaner agent 18, like small systems for household use of ozone cleaner agent 18, to large systems for commercial or industrial uses and volumes of ozone cleaner agent 18. Ozone cleaner agent 18 may be configured to be 99.99% effecting for disinfecting, cleaning, sanitizing, or the like. As such, ozone disinfecting system 10 may be configured so that specified cycle time 28 that ozone cleaning agent 18 is created by cycling fluid 24 between water holding tank 12 and ozone holding tank 17 may be configured to maintain ozone cleaning agent 18 to be 99.99% effective for disinfecting, cleaning, sanitizing, or the like. Ozone cleaning agent 18 may be ozonated water. Ozonated water may be widely used by water treatment utilities to kill bacteria and to reduce the incidence of waterborne infectious disease, wherein ozone disinfection disrupts microbial activity through three primary mechanisms, direct oxidation and destruction of the cell wall, secondary oxidizing reactions with the by-products of ozone decomposition, and damage to the cellular materials (nucleic and intercellular constituents). Prior to the instant disclosure, ozone (O3), or ozonated water, that was intended for disinfecting was typically generated at the point of use because it is unstable and rapidly decomposes to molecular oxygen (O2) after generation. The instant disclosure solves this issue by providing a mechanism, means and/or method to recycle or cycle the ozone or ozone cleaner agent 18 at specified time periods to maintain its effectiveness.

Wipe dispenser 32 may be included in select embodiments of ozone disinfecting system 10. See FIGS. 1, 2, 3, 4, 5, 7, 9, and 10. Wipe dispenser 32 may be for providing a plurality of wipes 36 saturated or coated with ozone cleaning agent 18. Whereby, the provided wipes 36 from ozone disinfecting system 10 may be configured for disinfecting, cleaning, sanitizing, the like, etc. Wipe dispenser 32 may include any parts, components, mechanisms, or means for saturating or coating plurality of wipes 36 with ozone cleaning agent 18 for configuring wipes 36 for disinfecting, cleaning, sanitizing, the like, etc. In select embodiments, as shown in the Figures, wipe dispenser 32 may include wipe holder 34 housed in ozone holding tank 17. Wipe holder 34 may be configured to hold plurality of wipes 36 submerged in ozone cleaning agent 18 that is cycled through ozone holding tank 17. Whereby, ozone disinfecting system 10 may be configured to maintain the plurality of wipes 36 at 99.99% effective for disinfecting, cleaning, sanitizing, the like, etc.

Spigot 38 may be included in select embodiments of ozone disinfecting system 10. See FIGS. 1, 3, 4, 5, 6, 7 and 9. Spigot 38 may be used and configured for providing a means to remove ozone cleaner agent 18 from ozone disinfecting system 10, like for filling cleaning bottles, mop buckets, saturating rags, cleaning hands, the like, etc. Spigot 38 may be positioned anywhere on disinfecting system 10 for providing a means to remove ozone cleaner agent 18 from ozone disinfecting system 10. Spigot 38 may be in communication with ozone holding tank 17. Spigot 38 may be configured for removing ozone cleaner agent 18 from ozone holding tank 17, like for filling separate cleaning containers with ozone cleaning agent 18. In select embodiments, spigot 38 may be connected to drain conduit 40. Drain conduit 40 may be configured to move fluid from drain 20 of ozone holding tank 17 to water holding tank 12. The separate cleaning containers filled from spigot 38 may be configured for aiding in disinfecting, cleaning, sanitizing, or the like, with ozone cleaning agent 18. As examples, and clearly not limited thereto, the separate cleaning containers may include, but are not limited thereto, bottle 42, spray bottle 44, bucket 46, mop bucket 48, basin 50, container 52, the like, and/or combinations thereof.

Power source 54 may be included with ozone disinfecting system 10. See FIGS. 1, 2, 3, 4, 5, 9, and 10. Power source 54 may be to provide power for powering ozone disinfecting system 10. Power source 54 may be any power source configured for powering ozone disinfecting system 10, including, but not limited to, powering controller 26, pump 22, drain 20, and ozone generating machine 16. As shown in the Figures, power source 54 may be, but is not limited to, wired power source 56, battery power source 58, the like, and combinations thereof. Wiring 62 may be included in ozone disinfecting system 10. Wiring 62 may be configured to provide communication between, but not limited to, power source 54, controller 26, pump 22, ozone generating machine 16, and drain 20.

Fluid lines 64 may be included with ozone generator system 10. See FIGS. 1, 3, 4, 5, and 7. Fluid lines 64 may be for moving and cycling fluid 24 (i.e. water 14, ozone cleaning agent 18, and/or mixtures thereof) through ozone disinfecting system 10. As such, fluid lines 64 may be for moving and cycling fluid 24 back and forth between water holding tank 12, pump 22, ozone generator machine 16, and ozone holding tank 17. Fluid lines may be designed, sized and configured for various sizes and configurations of ozone disinfecting system 10. In select embodiments, fluid lines 64 may include first fluid line 66, second fluid line 72. First fluid line 66 may be from approximate bottom 68 of water holding tank 12 to pump inlet 70 of pump 22. Second fluid line 72 may be from pump outlet 74 of pump 22 to ozone generator inlet 76 of ozone generating machine 16. In select embodiments, nozzle 84 may also be included in ozone holding tank 17. Nozzle 84 in ozone holding tank 17 may be configured to spray ozone cleaner agent 18 created by ozone generating machine 16 into ozone holding tank 17, like for saturating or coating plurality of wipes 36 positioned therein. Drain conduit 40 may also be included as fluid lines 64. Drain conduit 40 may be configured to move fluid 24 from drain 20 of ozone holding tank 17 to water holding tank 16, like via gravity.

Stand 88 may be included in select embodiments of ozone disinfecting system 10. See FIGS. 1, 3, 4, 5, 7, 9, and 10. Stand 88 may be configured to hold water holding tank 12 above pump 22 and controller 26. Stand 88 may include a flat surface for holding water holding tank 12 and a plurality of legs attached to the flat surface for positioning the flat surface above pump 22 and controller 26.

Referring now specifically to FIGS. 2-5, in select embodiments of the disclosure, ozone disinfecting system 10 may be configured for and incorporated in self-contained mobile wipe dispenser unit 100. Self-contained mobile wipe dispenser unit 100 may be configured for dispensing sanitizing wipes 36 soaked in ozone cleaner agent 18 cycled through ozone holding tank 17. As such, in another aspect, the instant disclosure embraces self-contained mobile wipe dispenser unit 100. Self-contained mobile wipe dispenser 100 may generally include ozone disinfecting system 10 in any of the various embodiments and/or combinations of embodiments shown and/or described herein. Accordingly, ozone disinfecting system 10 of self-contained mobile wipe dispenser 100 may generally include water holding tank 12, ozone generator machine 16, ozone holding tank 17, drain 20, pump 22, and controller 26. Water holding tank 12 may be configured to hold water 14 for use by ozone disinfecting system 10 inside of self-contained mobile wipe dispenser 100. Ozone generator machine 16 may be configured to convert water 14 into ozone cleaner agent 18. Ozone holding tank 17 may be configured to hold ozone cleaner agent 18 created by ozone generator machine 16 inside of self-contained mobile wipe dispenser 100. Drain 20 may be configured to drain fluid 24 from ozone holding tank 17 to water holding tank 12. Pump 22 may be configured to cycle fluid 24 from water holding tank 12 to ozone generator machine 16, and into ozone holding tank 17. Wherein, when fluid 24 is cycled, fluid 24 includes water 14 moving from water holding tank 12 to ozone generator machine 16, and fluid 24 includes ozone cleaner agent 18 moving from ozone generator machine 16 to ozone cleaner holding tank 17. Controller 26 may be configured to control pump 22, ozone generator machine 16, and drain 20. Wherein, controller 26 may control pump 22, ozone generator machine 16 and drain 20 to create ozone cleaner agent 18 from water 14 and cycle it between water holding tank 12 and ozone holding tank 17 at specified cycle time 28 inside of self-contained mobile wipe dispenser 100. One feature of self-contained mobile wipe dispenser unit 100 may be that it can be configured for dispensing sanitizing wipes 36 soaked in ozone cleaner agent 18 that is cycled through ozone holding tank 17.

Self-contained mobile wipe dispenser 100 may include wipe dispenser 32. Wipe dispenser 32 of self-contained mobile wipe dispenser 100 may be for providing plurality of wipes 36 saturated or coated with ozone cleaning agent 18. Whereby, the provided wipes 36 from self-contained mobile wipe dispenser 100 may be configured for disinfecting, cleaning, sanitizing, the like, etc. Wipe dispenser 32 may include any parts, components, mechanisms, or means for saturating or coating plurality of wipes 36 with ozone cleaning agent 18 for configuring wipes 36 for disinfecting, cleaning, sanitizing, the like, etc. In select embodiments, as shown in the Figures, wipe dispenser 32 may include wipe holder 34 housed in ozone holding tank 17 inside of self-contained mobile wipe dispenser 100. Wipe holder 34 may be configured to hold plurality of wipes 36 submerged in ozone cleaning agent 18 that is cycled through ozone holding tank 17. Whereby, self-contained mobile wipe dispenser 100 may be configured to maintain the plurality of wipes 36 at 99.99% effective for disinfecting, cleaning, sanitizing, the like, etc.

As shown in FIGS. 2-5, housing 102 may be included with self-contained mobile wipe dispenser unit 100. Housing 102 may be configured for housing ozone disinfecting system 10 inside of self-contained mobile wipe dispenser unit 100. In select embodiments, housing 102 may include substantially cylindrically shaped vessel 104. Substantially cylindrically shaped vessel 104 may have open top 106 and closed bottom 108. Ozone disinfecting system 10 may be positioned on closed bottom 108 inside of substantially cylindrically shaped vessel 104 of housing 102. Access door 110 may be included in substantially cylindrically shaped vessel 104. Access door 110 may be configured for accessing ozone disinfecting system 10 inside of substantially cylindrically shaped vessel 104 of self-contained mobile wipe dispenser unit 100. Shelf 112 may also be included inside of substantially cylindrically shaped vessel 104. Shelf 112 may be configured to hold ozone holding tank 17 inside of substantially cylindrically shaped vessel 104 in position 116 where top 114 of ozone holding tank 17 may be positioned approximate open top 106 of substantially cylindrically shaped vessel 104. Removable lid 118 may also be included with substantially cylindrically shaped vessel 104 of self-contained mobile wipe dispenser unit 100. Removable lid 118 may be configured for covering open top 106 of substantially cylindrically shaped vessel 104. Removable lid 118 may be configured to be removed for accessing wipe dispenser 32 and ozone holding tank 17 positioned on shelf 112. Removable lid 118 may include wipe opening 120 configured for pulling one of the plurality of wipes 36 at a time from wipe dispenser 32.

Spigot 38 may also be included in select embodiments of self-contained mobile wipe dispenser unit 100. Spigot 38 may be in communication with ozone holding tank 17. Spigot 38 may be configured for removing ozone cleaner agent 18 from ozone holding tank 17, like for filling separate cleaning containers with ozone cleaning agent 18, dampening wipes or rags with ozone cleaning agent 18, the like, etc. Spigot 38 may be positioned anywhere on or in self-contained mobile wipe dispenser unit 100. In select embodiments of self-contained mobile wipe dispenser unit 100, spigot 38 may be positioned where it can be accessed through access door 110 of substantially cylindrically shaped vessel 104.

Power source 54 may also be included with self-contained mobile wipe dispenser unit 100. Power source 54 may be configured for powering ozone disinfecting system 10 inside of self-contained mobile wipe dispenser unit 100, including, but not limited to, controller 26, pump 22, drain 20, and/or ozone generating machine 16 of ozone disinfecting system 10. As shown in FIGS. 2-5, in select embodiments, power source 54 may be wired power source 56 where self-contained mobile wipe dispenser unit 100 is plugged into an outlet for powering self-contained mobile wipe dispenser unit 100. Also, as shown in FIGS. 2-5, in select embodiments, power source 54 may be battery power source 58 where self-contained mobile wipe dispenser unit 100 may be mobile and put in any desired position without the need for an outlet near by. Also, as shown in FIGS. 2-5, in select possibly preferred embodiments, power source 54 may include both wired power source 56 and battery power source 58 for allowing powering self-contained mobile wipe dispenser unit 100 to be either plugged into a nearby outlet or to be mobile for putting it any desired position an run off battery powered source 58.

Referring now to FIGS. 6-10, in select embodiments of the disclosure, ozone disinfecting system 10 may be configured for and incorporated in self-contained mobile cleaning cart 200. Self-contained mobile cleaning cart 200 may be configured for providing ozone cleaner agent 18 to separate cleaning containers, for dispensing sanitizing wipes 36, the like, and/or combinations thereof. As such, in another aspect, the instant disclosure embraces self-contained mobile cleaning cart 200. Self-contained mobile cleaning cart 200 may generally include ozone disinfecting system 10 in any of the various embodiments and/or combinations of embodiments shown and/or described herein. Accordingly, ozone disinfecting system 10 of self-contained mobile cleaning cart 200 may generally include water holding tank 12, ozone generator machine 16, ozone holding tank 17, drain 20, pump 22, and controller 26. Water holding tank 12 may be configured to hold water 14 for use by ozone disinfecting system 10 inside of self-contained mobile cleaning cart 200. Ozone generator machine 16 may be configured to convert water 14 into ozone cleaner agent 18. Ozone holding tank 17 may be configured to hold ozone cleaner agent 18 created by ozone generator machine 16 inside of self-contained mobile cleaning cart 200. Drain 20 may be configured to drain fluid 24 from ozone holding tank 17 to water holding tank 12. Pump 22 may be configured to cycle fluid 24 from water holding tank 12 to ozone generator machine 16, and into ozone holding tank 17. Wherein, when fluid 24 is cycled, fluid 24 includes water 14 moving from water holding tank 12 to ozone generator machine 16, and fluid 24 includes ozone cleaner agent 18 moving from ozone generator machine 16 to ozone cleaner holding tank 17. Controller 26 may be configured to control pump 22, ozone generator machine 16, and drain 20. Wherein, controller 26 may control pump 22, ozone generator machine 16 and drain 20 to create ozone cleaner agent 18 from water 14 and cycle it between water holding tank 12 and ozone holding tank 17 at specified cycle time 28 inside of self-contained mobile cleaning cart 200.

As shown in FIGS. 6-10, cart device 202 may be included with self-contained mobile cleaning cart 200. Cart device 202 may be configured for housing ozone disinfecting system 10 for self-contained mobile cleaning cart 200. Cart device 202 may generally include base 204 with a plurality of wheels 206 attached thereto configured for rolling cart device 202. Enclosure 208 may be positioned on base 204. Enclosure 208 may be sized and configured for enclosing ozone disinfecting system 10 on cart device 202 of self-contained mobile cleaning cart 200. In select embodiments, enclosure 208 may include front door 210, back door 212, and/or top frame 214. Front door 210 may be configured for accessing ozone disinfecting system 10, like for accessing a front side of ozone disinfecting system 10. Back door 212 may also be configured for accessing ozone disinfecting system 10, like for accessing a back side of ozone disinfecting system 10. Top frame 214 may have opening 216, top lid 218, and a plurality of mounts 220. Top lid 218 may be configured to be opened for accessing ozone holding tank 17 of ozone disinfecting system 10 through opening 216. Opening 216 of top frame 214 may be configured to hold ozone holding tank 17 in position 116 above water holding tank 12, where lip 222 of ozone holding tank 17 may fit on top of top frame 214 and around opening 216. The plurality of mounts 220 of top frame 214 may be configured for mounting various cleaning accessories, or the like, including, but clearly not limited thereto, bottle 42, spray bottle 44, mop 221, basin 50, container 52, the like, or any various combinations thereof.

Drawer 224 may be included in select embodiments of self-contained mobile cleaning cart 200. Drawer 224 may be positioned below base 204 of cart device 202. Drawer 224 may be configured for housing controller 26 of ozone disinfecting system 10.

Spigot 38 may also be included in select embodiments of self-contained mobile cleaning cart 200. Spigot 38 may be in communication with ozone holding tank 17. Spigot 38 may be configured for removing ozone cleaner agent 18 from ozone holding tank 17, like for filling separate cleaning containers with ozone cleaning agent 18, dampening wipes or rags with ozone cleaning agent 18, the like, etc. Spigot 38 may be positioned anywhere on or in self-contained mobile cleaning cart 200. In select embodiments of self-contained mobile cleaning cart 200, spigot 38 may be positioned through enclosure 208 where it can be accessed outside of enclosure 208 of cart device 202. This may provide for easy access to spigot 38 for easily filling separate cleaning containers with ozone cleaning agent 18, dampening wipes or rags with ozone cleaning agent 18, the like, etc.

Mop bucket 225 may be included in select embodiments of self-contained mobile cleaning cart 200. Mop bucket 225 may be included with of self-contained mobile cleaning cart 200 for providing a basin or the like for mop 221, or the like. In select embodiments, mop bucket 225 may be positioned on base 204 on first side 226 of enclosure 208.

Spare water tank 228 may be included in select embodiments of self-contained mobile cleaning cart 200. Spare water tank 228 may be configured to hold extra of water 14 for ozone disinfecting system 10. Spare water tank 228 may be positioned anywhere on cart device 202. In select embodiments, as shown in the Figures, spare water tank 228 may be positioned on base 204 on second side 230 of enclosure 208.

Power source 54 may also be included with self-contained mobile cleaning cart 200. Power source 54 may be configured for powering ozone disinfecting system 10 inside of self-contained mobile cleaning cart 200, including, but not limited to, controller 26, pump 22, drain 20, and/or ozone generating machine 16 of ozone disinfecting system 10. As shown in FIGS. 6-10, in select embodiments, power source 54 may be battery power source 58 where self-contained mobile wipe dispenser unit 100 may be mobile and put in any desired position without the need for an outlet near by.

In another aspect, the present disclosure embraces a method of making ozone cleaner agent 18 in any of the various embodiments and/or combination of embodiments shown and/or described herein.

In another aspect, the present disclosure embraces a method of making disinfecting wipes 36 in any of the various embodiments and/or combination of embodiments shown and/or described herein.

In sum, the present disclosure embraces ozone disinfecting system 10 and devices (like self-contained mobile wipe dispenser unit 100 and/or self-contained mobile cleaning cart 200) configured to convert water 14 into ozone cleaner agent 18 for disinfecting, cleaning, sanitizing, the like, etc. Ozone cleaner agent 18 may have a limited shelf time, so ozone disinfecting system 10 the included time circulation unit is critical. This timed circulation feature of ozone disinfecting system 10 may enable it to provide ozone cleaner agent 18 and/or sanitizing wipes 36 at any time with just adding water. Ozone disinfecting system 10 may provide the ability to produce such ozone cleaner agent 18 and/or sanitizing wipes 36 with the disinfecting power of 99.9% in a self-contained mobile unit with no chemicals or VOCs. As an example, and clearly not limited thereto, ozone disinfecting system 10 may have the following features and/or benefits:

Can produce 720,000 gallons of disinfectant using any water to produce ozone cleaning agent 18.

Calculating with 30% of waste or 504,000 gallons of disinfectant.

Cost of the average 1 gallon of disinfectant=$19.67 ($19.67×504,000 gallons=$9,676,800 for chemicals).

Cost effective: using only H2O and a little electricity to provide a safe green way to clean hands, surfaces, interiors with no chemicals, VOCs, or chemical residue.

Reducing our harmful chemicals or VOCs in the air and on our surfaces via bring aqueous O3 to you and where you need it.

Has the same disinfecting powers and is 99.9% effective.

Reduces our need for plastic bottles and containers as the disclosed units are self-contained, creates the ability to produce a healthy disinfectant wipes with O3 disinfectant in quantities any place as long as you have water, electrically and the disclosed mobile unit.

Stand-alone disinfecting manufacturing station only limited to the ability of water & electricity.

Cost effective: using only H20 and a little electricity to provide a safe green way to clean hard surfaces, interiors with no chemicals, VOCs, or chemical residue.

Reducing our harmful chemicals or VOCs in the air and on our surfaces via bringing aqueous 03 to you and where you need it vs attached to you and where you need it vs. attached to a wall unit.

Has the same disinfecting powers as 99.9% effective.

Reduces our need for plastic bottles and containers as the disclosed units are self-contained, and the bottles or containers can be recycled with the disclosed ozone disinfecting system 10 and devices.

Creates the ability to produce a healthy disinfectant O3 disinfectant in qualities any place as long as you have water, electricity and the disclosed ozone disinfecting system 10 and/or devices.

Stand-alone disinfecting manufacturing station only limited to the ability of water if you need 100 gallons to disinfect, you have the ability to produce what you need on demand.

Ability to produce endless gallons of disinfecting 99.9% O3 with a self-contained mobile unit with no chemicals or VOCs.

Sanitizing wipes 89.95/6=$15.00 per tube 6"×6.75" size/240 wipes per tube=0.0625 cents per wipe. Kills 99.9% of most common germs. Active ingredient Benzalkonium Chloride 13%. Wellness center wipes—$139.95/4=$34.98 per tube 9"×6" size 1150 wipes per tube.=0.03 cents per wipe. Active ingredients: N-Alkyl (60% C 14, 30% CI 5, 5% C 12, 5% C 18) dimethyl benzyl ammonium chloride . . . 0.105%. N-Alkyl (68% C12, 32% C 14) dimethyl ethylenbenzyl ammonium chloride . . . 0.105%. Antibacterial & Disinfecting $109.95/4=$27.48 per tube 6"×8.5" size/800 wipes per tube=0.035 cents per wipe. Kills 99.9% of most common germs. Active ingredients: Alkyl (60% C14, 30% C 16, 5% C 12, 5% C18) dimethyl benzyl ammonium chloride . . . 0.14% N-Alkyl (68% C 12, 3 2% C14) di methyl ethylenbenzyl ammonium chloride . . . 0.14%. Inert ingredients: 99.72%.

EXAMPLE

An example self-contained mobile wipe dispenser unit 100 including ozone disinfecting system 10 may be constructed with the following parts:

Water Pump 22
Custom Main water reservoir stand 88
Push-to-connect 900 elbow's for ⅜ OD tube
Push-to-connect ST for ⅜" tube
Firm polyurethane tubing ⅜ od with ¼" Id (OPAQUE White)
Plastic pipe fitting for ⅜ NPT female
⅜ push-to-connect drain value for re-fill of main reservoir 12
Custom plastic pipe fitting for drain 20 in towel reservoir 17
Custom machined fitting for water tip nozzle 84
Eco-friendly ozone disinfecting machine 16
Custom towel container 34 for ozone filled towelette or wipes 36
3/21" drain hose/fitting for return of water to lower main reserve 12
Stainless steel housing 102 for ozone towelette system
On/off switch for controller 26
Timer switch for controller 26
0.250 cord fitting for wired powered source 56

Although the present disclosure has been illustrated and described herein with reference to preferred embodiments and specific examples thereof, it will be readily apparent to those of ordinary skill in the art that other embodiments and examples may perform similar functions and/or achieve like results. All such equivalent embodiments and examples are with the spirit and scope of the present disclosure, are contemplated thereby, and are intended to be covered by the following general description.

In the specification and/or figures, typical embodiments of the disclosure have been disclosed. The present disclosure is not limited to such exemplary embodiments. The use of the term "and/or" includes any and all combinations of one or more of the associated listed items. The figures are schematic representations and so are not necessarily drawn to scale. Unless otherwise noted, specific terms have been used in a generic and descriptive sense and not for purposes of limitation.

The foregoing description and drawings comprise illustrative embodiments. Having thus described exemplary embodiments, it should be noted by those skilled in the art that the within disclosures are exemplary only, and that various other alternatives, adaptations, and modifications may be made within the scope of the present disclosure. Merely listing or numbering the steps of a method in a certain order does not constitute any limitation on the order of the steps of that method. Many modifications and other embodiments will come to mind to one skilled in the art to which this disclosure pertains having the benefit of the teachings presented in the foregoing descriptions and the associated drawings. Although specific terms may be employed herein, they are used in a generic and descriptive sense only and not for purposes of limitation. Accordingly, the present disclosure is not limited to the specific embodiments illustrated herein but is limited only by the following claims.

The invention claimed is:

1. An ozone disinfecting system comprising:
a water holding tank configured to hold water;
an ozone generator machine configured to convert the water into an ozone cleaner agent, the ozone cleaner agent is an ozonated water created from the water via the ozone generator machine;
an ozone holding tank configured to hold the ozone cleaner agent created by the ozone generator machine;
a drain configured to drain fluid from the ozone holding tank to the water holding tank;
a pump configured to cycle the fluid from the water holding tank to the ozone generator machine, and into the ozone holding tank, wherein when the fluid is cycled, the fluid includes the water moving from the water holding tank to the ozone generator machine, and the fluid includes the ozone cleaner agent moving from the ozone generator machine to the ozone cleaner holding tank;

fluid lines, the fluid lines including:
a first fluid line from approximate a bottom of the water holding tank to a pump inlet of the pump;
a second fluid line from a pump outlet of the pump to an ozone generator inlet of the ozone generating machine;
a nozzle in the ozone holding tank configured to spray the ozone cleaner agent created by the ozone generating machine into the ozone holding tank; and
a drain conduit, the drain conduit is configured to move the fluid from the drain of the ozone holding tank to the water holding tank via gravity; and
a controller configured to control the pump, the ozone generator machine, and the drain, wherein the controller controls the pump, the ozone generator machine and the drain to create the ozone cleaner agent from the water and cycle it between the water holding tank and the ozone holding tank at a specified cycle time, where the same fluid is cycled between the ozone holding tank and the water holding tank, and wherein the specified cycle time is configured to maintain the fluid in the ozone holding tank to be in the form of ozone;
the ozone holding tank including:
an open portion configured for removing the ozone cleaner agent from the ozone holding tank for external use of the ozone cleaner agent for disinfecting, cleaning, or sanitizing;
a spigot configured for removing the ozone cleaner agent from the ozone holding tank for external use of the ozone cleaner agent for disinfecting, cleaning, or sanitizing; or
a combination thereof.

2. The ozone disinfecting system of claim 1 is configured for making the ozone cleaning agent on demand anytime by just adding the water to the water holding tank, wherein the ozone cleaner agent created from the water by the ozone generator machine is made with no chemicals or volatile organic compounds and is configured for disinfecting, cleaning, or sanitizing.

3. The ozone disinfecting system of claim 2, wherein the ozone cleaner agent created on demand from the water by the ozone generator machine is configured to be 99.99% effecting for disinfecting, cleaning, or sanitizing.

4. The ozone disinfecting system of claim 3, wherein the specified cycle time that the ozone cleaning agent is created on demand by cycling the fluid between the water holding tank and the ozone holding tank is configured to maintain the ozone cleaning agent to be 99.99% effective for disinfecting, cleaning, or sanitizing.

5. The ozone disinfecting system of claim 4, wherein the controller including an adjustable timer configured to adjust the specified cycle time that the ozone cleaning agent is created on demand by cycling the fluid between the water holding tank and the ozone holding tank, wherein the adjustable timer is configured to adjust the specified cycle time between a group consisting of:
every 30 minutes or more;
every 15 minutes or more;
every 10 minutes or more; and
every 5 minutes or more.

6. The ozone disinfecting system of claim 1 further comprising a wipe dispenser.

7. The ozone disinfecting system of claim 6, wherein the wipe dispenser includes a wipe holder housed in the ozone holding tank.

8. The ozone disinfecting system of claim 7, wherein the wipe holder is configured to hold a plurality of wipes submerged in the ozone cleaning agent that is cycled through the ozone holding tank, whereby the plurality of wipes are configured to be maintained at 99.99% effective for disinfecting, cleaning, or sanitizing.

9. The ozone disinfecting system of claim 1 wherein, the spigot is configured for removing the ozone cleaner agent from the ozone holding tank for filling a separate cleaning container with the ozone cleaning agent.

10. The ozone disinfecting system of claim 9, wherein the spigot is connected to a drain conduit, the drain conduit is configured to move the fluid from the drain of the ozone holding tank to the water holding tank.

11. The ozone disinfecting system of claim 9, wherein the separate cleaning container is configured for aiding in disinfecting, cleaning or sanitizing with the ozone cleaning agent, where the separate cleaning container is a bottle, a spray bottle, a bucket, a mop bucket, a basin, or a container.

12. The ozone disinfecting system of claim 1 further comprising a power source configured to power the controller, the pump, the drain, and the ozone generating machine.

13. The ozone disinfecting system of claim 12, wherein the power source is selected from a group consisting of: a wired power source; a battery power source; and a combination thereof.

14. The ozone disinfecting system of claim 12 further comprising:
wiring configured to provide communication between the power source, the controller, the pump, the ozone generating machine, and the drain.

15. The ozone disinfecting system of claim 1 further comprising a stand, the stand being configured to hold the water holding tank above the pump and the controller.

16. The ozone disinfecting system of claim 1 being configured for:
a self-contained mobile wipe dispenser unit configured for dispensing sanitizing wipes soaked in the ozone cleaner agent cycled through the ozone holding tank; or
a self-contained mobile cleaning cart configured for providing the ozone cleaner agent to separate cleaning containers, for dispensing sanitizing wipes, or combinations thereof.

17. A self-contained mobile wipe dispenser unit comprising:
an ozone disinfecting system comprising:
a water holding tank configured to hold water;
an ozone generator machine configured to convert the water into an ozone cleaner agent, the ozone cleaner agent is an ozonated water created from the water via the ozone generator machine;
an ozone holding tank configured to hold the ozone cleaner agent created by the ozone generator machine;
a drain configured to drain fluid from the ozone holding tank to the water holding tank;
a pump configured to cycle the fluid from the water holding tank to the ozone generator machine, and into the ozone holding tank, wherein when the fluid is cycled, the fluid includes the water moving from the water holding tank to the ozone generator machine, and the fluid includes the ozone cleaner agent moving from the ozone generator machine to the ozone cleaner holding tank;
fluid lines, the fluid lines including:
a first fluid line from approximate a bottom of the water holding tank to a pump inlet of the pump;

a second fluid line from a pump outlet of the pump to an ozone generator inlet of the ozone generating machine;
a nozzle in the ozone holding tank configured to spray the ozone cleaner agent created by the ozone generating machine into the ozone holding tank; and
a drain conduit, the drain conduit is configured to move the fluid from the drain of the ozone holding tank to the water holding tank via gravity;
a controller configured to control the pump, the ozone generator machine, and the drain, wherein the controller controls the pump, the ozone generator machine and the drain to create the ozone cleaner agent from the water and cycle it between the water holding tank and the ozone holding tank at a specified cycle time, where the same fluid is cycled between the ozone holding tank and the water holding tank, and wherein the specified cycle time is configured to maintain the fluid in the ozone holding tank to be in the form of ozone; and
a wipe dispenser including a wipe holder housed in the ozone holding tank, the wipe holder is configured to hold a plurality of wipes submerged in the ozone cleaning agent that is cycled through the ozone holding tank, whereby the plurality of wipes are configured to be maintained at 99.99% effective for disinfecting, cleaning, or sanitizing;
the ozone holding tank including an open portion configured for removing the wipes from the ozone holding tank for external use of the wipes with the ozone cleaning agent for disinfecting, cleaning, or sanitizing.

18. The self-contained mobile wipe dispenser unit of claim 17 further comprising:
a housing configured for housing the ozone disinfecting system, the housing including:
a substantially cylindrically shaped vessel with an open top and a closed bottom, where the ozone disinfecting system is positioned on the closed bottom inside of the substantially cylindrically shaped vessel;
an access door in the substantially cylindrically shaped vessel configured for accessing the ozone disinfecting system inside of the substantially cylindrically shaped vessel;
a shelf inside of the substantially cylindrically shaped vessel, the shelf is configured to hold the ozone holding tank inside of the substantially cylindrically shaped vessel in a position where a top of the ozone holding tank is positioned approximate the open top of the substantially cylindrically shaped vessel; and
a removable lid configured for covering the open top of the substantially cylindrically shaped vessel, the removable lid is configured to be removed for accessing the wipe dispenser and ozone holding tank positioned on the shelf, the removable lid including a wipe opening configured for pulling one of the plurality of wipes at a time from the wipe dispenser;
a spigot in communication with the ozone holding tank, the spigot is configured for removing the ozone cleaner agent from the ozone holding tank for filling a separate cleaning container with the ozone cleaning agent, the spigot is positioned where it can be accessed through the access door of the substantially cylindrically shaped vessel; and
a power source configured to power the controller, the pump, the drain, and the ozone generating machine of the ozone disinfecting system for the self-contained mobile wipe dispenser unit;
wherein, the self-contained mobile wipe dispenser unit is configured for dispensing sanitizing wipes soaked in the ozone cleaner agent cycled through the ozone holding tank.

19. A self-contained mobile cleaning cart comprising:
an ozone disinfecting system comprising:
a water holding tank configured to hold water;
an ozone generator machine configured to convert the water into an ozone cleaner agent, the ozone cleaner agent is an ozonated water created from the water via the ozone generator machine;
an ozone holding tank configured to hold the ozone cleaner agent created by the ozone generator machine;
a drain configured to drain fluid from the ozone holding tank to the water holding tank;
a pump configured to cycle the fluid from the water holding tank to the ozone generator machine, and into the ozone holding tank, wherein when the fluid is cycled, the fluid includes the water moving from the water holding tank to the ozone generator machine, and the fluid includes the ozone cleaner agent moving from the ozone generator machine to the ozone cleaner holding tank;
fluid lines, the fluid lines including:
a first fluid line from approximate a bottom of the water holding tank to a pump inlet of the pump;
a second fluid line from a pump outlet of the pump to an ozone generator inlet of the ozone generating machine;
a nozzle in the ozone holding tank configured to spray the ozone cleaner agent created by the ozone generating machine into the ozone holding tank; and
a drain conduit, the drain conduit is configured to move the fluid from the drain of the ozone holding tank to the water holding tank via gravity;
a controller configured to control the pump, the ozone generator machine, and the drain, wherein the controller controls the pump, the ozone generator machine and the drain to create the ozone cleaner agent from the water and cycle it between the water holding tank and the ozone holding tank at a specified cycle time, where the same fluid is cycled between the ozone holding tank and the water holding tank, and wherein the specified cycle time is configured to maintain the fluid in the ozone holding tank to be in the form of ozone;
a cart device configured for housing the ozone disinfecting system; and
the ozone holding tank on the cart device including:
an open portion configured for removing the ozone cleaner agent from the ozone holding tank on the cart device for external use of the ozone cleaner agent for disinfecting, cleaning, or sanitizing;
a spigot configured for removing the ozone cleaner agent from the ozone holding tank on the cart device for external use of the ozone cleaner agent for disinfecting, cleaning, or sanitizing; or
a combination thereof.

20. The self-contained mobile cleaning cart of claim 19 further comprising:
the cart device including:
a base with a plurality of wheels attached thereto configured for rolling the cart device an enclosure positioned on the base, the enclosure is sized and configured for enclosing the ozone disinfecting system, the enclosure including:
  a front door configured for accessing the ozone disinfecting system;
  a back door configured for accessing the ozone disinfecting system; and
  a top frame with an opening, a top lid, and a plurality of mounts, the top lid is configured to be opened for accessing the ozone holding tank of the ozone disinfecting system through the opening, the opening of the top frame is configured to hold the ozone holding tank in a position above the water holding tank, where a lip of the ozone holding tank fits on top of the top frame and around the opening, the plurality of mounts of the top frame are configured for mounting a bottle, a spray bottle, a mop, a basin, a container, or a combination thereof;
a drawer positioned below the base, the drawer is configured for housing the controller of the ozone disinfecting system;
the spigot is in communication with the ozone holding tank, the spigot is configured for removing the ozone cleaner agent from the ozone holding tank for filling a separate cleaning container with the ozone cleaning agent, the spigot is positioned through the enclosure where it can be accessed outside of the enclosure;
a mop bucket positioned on the base on a first side of the enclosure;
a spare water tank positioned on the base on a second side of the enclosure, the spare water tank is configured to hold extra of the water for the ozone disinfecting system; and
a power source configured to power the controller, the pump, the drain, and the ozone generating machine of the ozone disinfecting system for the self-contained mobile wipe dispenser unit.

21. A self-contained mobile wipe dispenser unit comprising:
  an ozone disinfecting system comprising:
    a water holding tank configured to hold water;
    an ozone generator machine configured to convert the water into an ozone cleaner agent;
    an ozone holding tank configured to hold the ozone cleaner agent created by the ozone generator machine;
    a drain configured to drain fluid from the ozone holding tank to the water holding tank;
    a pump configured to cycle the fluid from the water holding tank to the ozone generator machine, and into the ozone holding tank, wherein when the fluid is cycled, the fluid includes the water moving from the water holding tank to the ozone generator machine, and the fluid includes the ozone cleaner agent moving from the ozone generator machine to the ozone cleaner holding tank;
    a controller configured to control the pump, the ozone generator machine, and the drain, wherein the controller controls the pump, the ozone generator machine and the drain to create the ozone cleaner agent from the water and cycle it between the water holding tank and the ozone holding tank at a specified cycle time;
  a wipe dispenser including a wipe holder housed in the ozone holding tank, the wipe holder is configured to hold a plurality of wipes submerged in the ozone cleaning agent that is cycled through the ozone holding tank, whereby the plurality of wipes are configured to be maintained at 99.99% effective for disinfecting, cleaning, or sanitizing;
  a housing configured for housing the ozone disinfecting system, the housing including:
    a substantially cylindrically shaped vessel with an open top and a closed bottom, where the ozone disinfecting system is positioned on the closed bottom inside of the substantially cylindrically shaped vessel;
    an access door in the substantially cylindrically shaped vessel configured for accessing the ozone disinfecting system inside of the substantially cylindrically shaped vessel;
    a shelf inside of the substantially cylindrically shaped vessel, the shelf is configured to hold the ozone holding tank inside of the substantially cylindrically shaped vessel in a position where a top of the ozone holding tank is positioned approximate the open top of the substantially cylindrically shaped vessel; and
    a removable lid configured for covering the open top of the substantially cylindrically shaped vessel, the removable lid is configured to be removed for accessing the wipe dispenser and ozone holding tank positioned on the shelf, the removable lid including a wipe opening configured for pulling one of the plurality of wipes at a time from the wipe dispenser;
  a spigot in communication with the ozone holding tank, the spigot is configured for removing the ozone cleaner agent from the ozone holding tank for filling a separate cleaning container with the ozone cleaning agent, the spigot is positioned where it can be accessed through the access door of the substantially cylindrically shaped vessel; and
  a power source configured to power the controller, the pump, the drain, and the ozone generating machine of the ozone disinfecting system for the self-contained mobile wipe dispenser unit; and
  wherein, the self-contained mobile wipe dispenser unit is configured for dispensing sanitizing wipes soaked in the ozone cleaner agent cycled through the ozone holding tank.

22. A self-contained mobile cleaning cart comprising:
  an ozone disinfecting system comprising:
    a water holding tank configured to hold water;
    an ozone generator machine configured to convert the water into an ozone cleaner agent;
    an ozone holding tank configured to hold the ozone cleaner agent created by the ozone generator machine;
    a drain configured to drain fluid from the ozone holding tank to the water holding tank;
    a pump configured to cycle the fluid from the water holding tank to the ozone generator machine, and into the ozone holding tank, wherein when the fluid is cycled, the fluid includes the water moving from the water holding tank to the ozone generator machine, and the fluid includes the ozone cleaner agent moving from the ozone generator machine to the ozone cleaner holding tank;
    a controller configured to control the pump, the ozone generator machine, and the drain, wherein the controller controls the pump, the ozone generator machine and the drain to create the ozone cleaner agent from the water and cycle it between the water holding tank and the ozone holding tank at a specified cycle time;
  a cart device configured for housing the ozone disinfecting system, the cart device including:

a base with a plurality of wheels attached thereto configured for rolling the cart device an enclosure positioned on the base, the enclosure is sized and configured for enclosing the ozone disinfecting system, the enclosure including:

a front door configured for accessing the ozone disinfecting system;

a back door configured for accessing the ozone disinfecting system; and a top frame with an opening, a top lid, and a plurality of mounts, the top lid is configured to be opened for accessing the ozone holding tank of the ozone disinfecting system through the opening, the opening of the top frame is configured to hold the ozone holding tank in a position above the water holding tank, where a lip of the ozone holding tank fits on top of the top frame and around the opening, the plurality of mounts of the top frame are configured for mounting a bottle, a spray bottle, a mop, a basin, a container, or a combination thereof;

a drawer positioned below the base, the drawer is configured for housing the controller of the ozone disinfecting system;

a spigot in communication with the ozone holding tank, the spigot is configured for removing the ozone cleaner agent from the ozone holding tank for filling a separate cleaning container with the ozone cleaning agent, the spigot is positioned through the enclosure where it can be accessed outside of the enclosure;

a mop bucket positioned on the base on a first side of the enclosure;

a spare water tank positioned on the base on a second side of the enclosure, the spare water tank is configured to hold extra of the water for the ozone disinfecting system; and a power source configured to power the controller, the pump, the drain, and the ozone generating machine of the ozone disinfecting system for the self-contained mobile wipe dispenser unit.

\* \* \* \* \*